(12) United States Patent
Baba et al.

(10) Patent No.: US 11,795,133 B2
(45) Date of Patent: Oct. 24, 2023

(54) PROCESS FOR PREPARING 6-ISOPROPENYL-3-METHYL-9-DECENYL ACETATE, AND INTERMEDIATES THEREFOR

(71) Applicant: Shin-Etsu Chemical Co., Ltd., Tokyo (JP)

(72) Inventors: Akihiro Baba, Niigata (JP); Takeshi Kinsho, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 90 days.

(21) Appl. No.: 17/368,996

(22) Filed: Jul. 7, 2021

(65) Prior Publication Data

US 2022/0017447 A1 Jan. 20, 2022

(30) Foreign Application Priority Data

Jul. 10, 2020 (JP) .................................. 2020-119194
Jan. 28, 2021 (JP) .................................. 2021-011957

(51) Int. Cl.
*C07C 67/08* (2006.01)

(52) U.S. Cl.
CPC .................................. *C07C 67/08* (2013.01)

(58) Field of Classification Search
CPC ......... C07C 67/08; C07C 17/16; C07C 21/19; C07C 29/09; C07C 29/10; C07C 29/103; C07C 33/02; C07C 41/48; C07C 43/303; C07C 67/24; C07C 69/145; C07C 69/24; G02B 26/004; G02B 26/0841; G02B 3/14;
(Continued)

(56) References Cited

U.S. PATENT DOCUMENTS 4,158,096 A 6/1979 Anderson

FOREIGN PATENT DOCUMENTS

JP S527427 A 1/1977

OTHER PUBLICATIONS

STN Doc (2 pages) (Year: 1984).*

(Continued)

*Primary Examiner* — Yevgeny Valenrod
*Assistant Examiner* — Blaine G Doletski
(74) *Attorney, Agent, or Firm* — Myers Bigel, P.A.

(57) ABSTRACT

The present invention provides a process for preparing 6-isopropenyl-3-methyl-9-decenyl acetate (5): wherein Ac represents an acetyl group, the process comprising steps of: subjecting a 2-methyl-2,6-heptadiene compound (1) having a leaving group X at position 1: wherein X represents an acyloxy group having 1 to 10 carbon atoms including the carbon atom of the carbonyl group, an alkanesulfonyloxy group having 1 to 10 carbon atoms, an arenesulfonyloxy group having 6 to 20 carbon atoms, or a halogen atom, to a nucleophilic substitution reaction with a 3-methylpentyl nucleophilic reagent (2) having a protected hydroxyl group at position 5: wherein M represents Li, $MgZ^1$, $ZnZ^1$, Cu, $CuZ^1$, or $CuLiZ^1$, wherein $Z^1$ represents a halogen atom or a $CH_2CH_2CH(CH_3)CH_2CH_2OR$ group, and R represents a protecting group for a hydroxyl group, to form a 6-isopropenyl-3-methyl-9-decene compound (3) having a protected hydroxyl group at position 1: wherein R is as defined above; subjecting the 6-isopropenyl-3-methyl-9-decene compound (3) having the protected hydroxyl group at position 1 to a deprotection reaction to form 6-isopropenyl-3-methyl-9-decenol (4); and acetylating 6-isopropenyl-3-methyl-9-decenol (4) to form 6-isopropenyl-3-methyl-9-decenyl acetate (5).

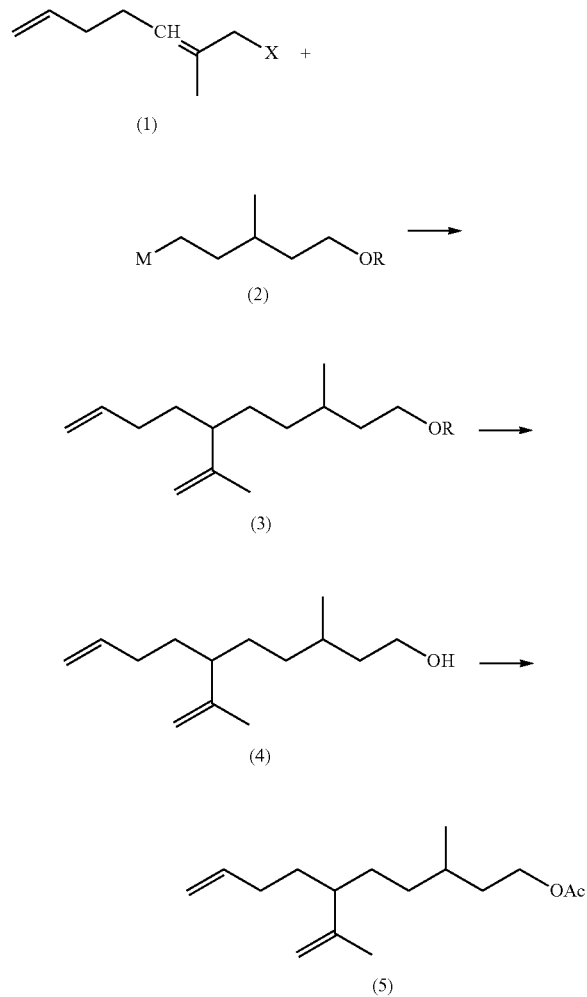

10 Claims, No Drawings

(58) Field of Classification Search
CPC . G02B 7/08; G02B 7/09; G03B 13/36; G03B 29/00; G03B 3/10; G03B 30/00; G03B 17/02; G03B 3/00; C07F 1/08; C07F 3/02; H05K 1/111; H05K 3/321; Y02P 20/55; H04N 23/55
See application file for complete search history.

(56) References Cited

OTHER PUBLICATIONS

Baudouy et al., Translated 1988 (Year: 1988).*
Baudouy et al., "Synthese diastereoselective d'une composante de la pheromone sexuelle de "l'ecaille rouge de californie" : l'acetate d'isopropenyl-6 methyl-3 decene-9 yle (3S, 6R)", Tetrahedron 44(2), 471-480 Published 1988 (Year: 1988).*
Harding et al. (Cyclization of 4-(trans-3,7-Cctadienyl)-3-methyl-2-cyclohexen-1-ol and 4-(trans,trans-7-Methyl-3,7,11-dodecatrienyl)-3-methyl-2-cyclohexen-1-ol, J. Amer. Chem. Soc., 98:8, pp. 2540-2549, Published 1974) (Year: 1974).*
Brady et al. (A Highly Stereoselective Synthesis of trans-Trisubstituted Olefinic Bonds, J. Amer. Chem. Soc., 90:11, pp. 2882-2889, Published May 1968) discloses the identical compound above (p. 2886 left column) (Year: 1968).*

Baudouy et al. "Synthese diastereoselective d'une composante de la pheromone sexuelle de "l'ecaille rouge de californie" : l'acetate d'isopropenyl-6 methyl-3 decene-9 yle (3S, 6R)" Tetrahedron, 44(2):471-480 (1988) (English translation of abstract).
Dragan et al. "Synthesis of the AI component of the red san jose scale sex pheromone" Organic Chemistry, 38:1038-1041 (1989).
Gieselmann et al. "Responses of Male California Red Scale to Sex Pheromone Isomers" Journal of Insect Physiology, 26(3): 179-182 (1980).
Kefalas et al. "Efficient Synthesis of the Aonidiella aurantii (Mask.) Sex Pheromone Component: (3S,6RS)-3-Methyl-6-(1-Methylethenyl)-9-decenyl Acetate" Synthesis, (6):644-646 (1995).
Becker et al. "New Synthesis of the California Red Scale Sex Pheromone" Tetrahedron, 44(14):4541-4546 (1988).
Database Caplus [Online] Database accession No. 1978: 136189 "Insecticidal and acaricidal cyclopropane carboxylates 11" (2 pages) (1978).
Extended European Search Report corresponding to European Patent Application No. 21184426.1 (9 pages) (dated Dec. 2, 2021).
Giacomina et al. "Construction of Enantioenriched Cyclic Compounds by Asymmetric Allylic Alkylation and Ring-Closing Metathesis" European Journal of Organic Chemistry, 2013(29):6710-6721 (2013).

* cited by examiner

PROCESS FOR PREPARING 6-ISOPROPENYL-3-METHYL-9-DECENYL ACETATE, AND INTERMEDIATES THEREFOR

TECHNICAL FIELD

The present invention relates to a process for preparing 6-isopropenyl-3-methyl-9-decenyl acetate, which is a sex pheromone substance of a citrus pest, California red scale (scientific name: Aonidiella aurantii), and intermediates therefor.

BACKGROUND ART

Insect sex pheromones are biologically active substances which are usually borne by females to attract males, and exhibit a high attracting activity in a small amount. Sex pheromones are widely utilized as a means for forecasting outbreaks of pests and confirming geographic spread (invasion into a specific area), and also as a means for controlling pests. Widely used methods for controlling pests include a mass trapping method, a lure-and-kill or attract-and-kill method, a lure-and-infect or attract-and-infect method, and a mating disruption method. A naturally occurred sex pheromones can be extracted from an insect individual only in a trace amount. Therefore, it is difficult to use a naturally occurred sex pheromone for a mating disruption method. Before practical use of a sex pheromone, it is required to artificially produce a sufficient amount of a sex pheromone for basic research and also for applications.

California red scale is a pest that has spread widely throughout the world to infest citrus. (3S,6R)-6-Isopropenyl-3-methyl-9-decenyl acetate is reported as a sex pheromone of California red scale (Non-Patent Literature 1 listed below). 6-Isopropenyl-3-methyl-9-decenyl acetate includes four isomers: (3R,6R)-6-isopropenyl-3-methyl-9-decenyl acetate, (3R,6S)-6-isopropenyl-3-methyl-9-decenyl acetate, (3S,6R)-6-isopropenyl-3-methyl-9-decenyl acetate, and (3S,6S)-6-isopropenyl-3-methyl-9-decenyl acetate. It is reported that California red scale is attracted also by a mixture of these four isomers (Non-Patent Literature 1 listed below).

A process for preparing 6-isopropenyl-3-methyl-9-decenyl acetate is reported. For example, in the following Non-Patent Literature 2, the process comprises oxidizing a trisubstituted double bond moiety of citronellol acetate with selenium dioxide and tert-butylhydroperoxide, chlorinating the introduced hydroxyl group with triphenylphosphine and carbon tetrachloride, and then subjecting the product to a nucleophilic substitution reaction to form (3S,6RS)-6-isopropenyl-3-methyl-9-decenyl acetate. In the following Non-Patent Literature 3, the process comprises preparing a sulfide compound from citronellol acetate, subjecting the sulfide compound to a 1,2-Stevens rearrangement reaction in the presence of a strong base with meta-chloroperbenzoic acid, oxidating the product with meta-chloroperbenzoic acid to prepare a sulfone compound, and then subjecting the sulfone compound to a trialkylation and a reductive elimination of sulfone to form 6-isopropenyl-3-methyl-9-decenyl acetate.

Further, a process for preparing (3S,6R)-6-isopropenyl-3-methyl-9-decenyl acetate is also reported in the following Non-Patent Literature 4, wherein the process comprises first eight steps including conversion of (−)-dihydrocarvone into a silylenol ether compound, ozone oxidation, reduction with sodium borohydride, and methylation of the carboxylic acid with diazomethane to synthesize (2S,5R)-5-isopropenyl-2-methyl-8-nonenyl iodide; and then four steps including preparing a nitrile compound using sodium cyanide.

LIST OF THE LITERATURES

Non-Patent Literatures

[Non-Patent Literature 1] M. J. GIESELMANN et al., J. Insect. Physiol. 26, 179 (1980)
[Non-Patent Literature 2] Panagiotis Kefalas et al., Synthesis. 644 (1995)
[Non-Patent Literature 3] V. A. Dragan et al., Russ. Chem. Bull. 38, 1038 (1989)
[Non-Patent Literature 4] R. Boudduy et al., Tetrahedron. 44, 471 (1988)

Problems to be Solved by the Invention

In the process described in Non-Patent Literature 2, selenium dioxide and tert-butylhydroperoxide used in the oxidation reaction of citronellol acetate cause waste which is toxic and environmentally high hazardous and are undesirable for environmental protection. The oxidation reaction may cause explosion and, therefore, is industrially less feasible. Moreover, the oxidation reaction gives a yield as low as 52%.

In the process described in Non-Patent Literature 3, meta-chloroperbenzoic acid used in the oxidation of a sulfide compound may cause explosion. Highly toxic hexamethylphosphoric triamide is used as a solvent in alkylation. These make the process industrially less feasible. The process consists of eight steps and gives a yield as low as 12.3%.

In the process described in Non-Patent Literature 4, synthesis of an intermediate, (2S,5R)-5-isopropenyl-2-methyl-8-nonenyl iodide, requires eight steps which include industrially less unfeasible ozone oxidation is carried out, and use is made of explosive and highly toxic diazomethane. Accordingly, the process is industrially unfavorable. Besides, the formation of (3 S,6R)-6-isopropenyl-3-methyl-9-decenyl acetate from (2S,5R)-5-isopropenyl-2-methyl-8-nonenyl iodide requires total four steps. Highly toxic sodium cyanide is used. These make the process industrially less feasible.

Thus, the aforesaid known processes seem to be very difficult to industrially prepare a sufficient amount of 6-isopropenyl-3-methyl-9-decenyl acetate.

SUMMARY OF THE INVENTION

The present invention has been made in these circumstances, and aims to provide a process for efficiently and industrially preparing 6-isopropenyl-3-methyl-9-decenyl acetate, without oxidation reaction, in a sufficient amount for biological or agricultural activity tests and/or for practical application.

As a result of the intensive researches to solve the problems, the present inventors have found a 2-methyl-2,6-heptadiene compound; that this compound may be used to industrially prepare 6-isopropenyl-3-methyl-9-decenyl acetate; and that the 2-methyl-2,6-heptadiene compound is a useful intermediate for the preparation of 6-isopropenyl-3-methyl-9-decenyl acetate. Thus, the present invention has been invented.

One aspect of the present invention provides a process for preparing 6-isopropenyl-3-methyl-9-decenyl acetate of the following formula (5):

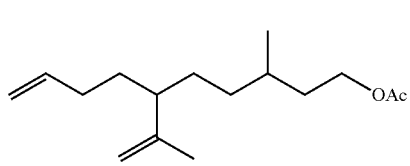

(5)

wherein Ac represents an acetyl group, the process comprising steps of:
subjecting a 2-methyl-2,6-heptadiene compound of the following general formula (1) having a leaving group X at position 1:

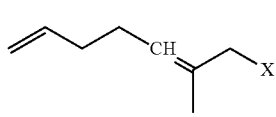

(1)

wherein X represents an acyloxy group having 1 to 10 carbon atoms including the carbon atom of the carbonyl group, an alkanesulfonyloxy group having 1 to 10 carbon atoms, an arenesulfonyloxy group having 6 to 20 carbon atoms, or a halogen atom, to a nucleophilic substitution reaction with a 3-methylpentyl nucleophilic reagent of the following general formula (2) having a protected hydroxyl group at position 5:

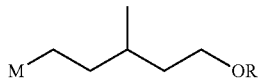

(2)

wherein M represents Li, MgZ$^1$, ZnZ$^1$, Cu, CuZ$^1$, or CuLiZ$^1$, wherein Z$^1$ represents a halogen atom or a $CH_2CH_2CH(CH_3)CH_2CH_2OR$ group, and R represents a protecting group for a hydroxyl group, to form a 6-isopropenyl-3-methyl-9-decene compound of the following general formula (3) having a protected hydroxyl group at position 1:

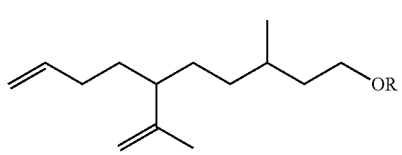

(3)

wherein R is as defined above;
subjecting the 6-isopropenyl-3-methyl-9-decene compound (3) having the protected hydroxyl group at position 1 to a deprotection reaction to form 6-isopropenyl-3-methyl-9-decenol of the following formula (4):

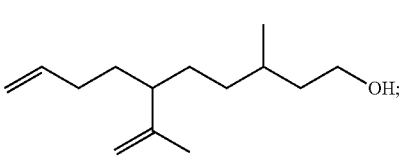

(4)

and
acetylating 6-isopropenyl-3-methyl-9-decenol (4) to form 6-isopropenyl-3-methyl-9-decenyl acetate (5).

Another aspect of the present invention provides a process for preparing 6-isopropenyl-3-methyl-9-decenyl acetate of the following formula (5):

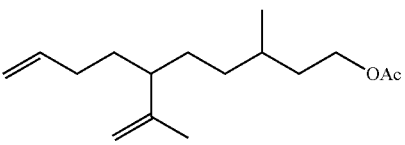

(5)

wherein Ac represents an acetyl group, the process comprising steps of:
subjecting a 2-methyl-2,6-heptadiene compound of the following general formula (1) having a leaving group X at position 1:

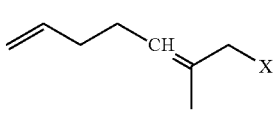

(1)

wherein X represents an acyloxy group having 1 to 10 carbon atoms including the carbon atom of the carbonyl group, an alkanesulfonyloxy group having 1 to 10 carbon atoms, an arenesulfonyloxy group having 6 to 20 carbon atoms, or a halogen atom, to a nucleophilic substitution reaction with a 3-methylpentyl nucleophilic reagent of the following general formula (2) having a protected hydroxyl group at position 5:

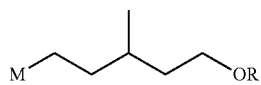

(2)

wherein M represents Li, MgZ$^1$, ZnZ$^1$, Cu, CuZ$^1$, or CuLiZ$^1$, wherein Z$^1$ represents a halogen atom or a $CH_2CH_2CH(CH_3)CH_2CH_2OR$ group, and R represents a protecting group for a hydroxyl group, to form a 6-isopropenyl-3-methyl-9-decene compound of the following general formula (3) having a protected hydroxyl group at position 1:

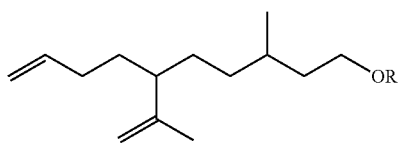

(3)

wherein R is as defined above; and
  subjecting the 6-isopropenyl-3-methyl-9-decene compound (3) having the protected hydroxyl group at position 1 to acetylation to form 6-isopropenyl-3-methyl-9-decenyl acetate (5).

Another aspect of the present invention provides a process for preparing 6-isopropenyl-3-methyl-9-decenyl acetate (5), the process further comprising a step of:
  converting the hydroxyl group of 2-methyl-2,6-heptadienol of the following formula (6):

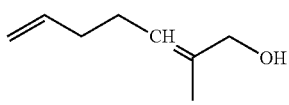

(6)

to X to form the 2-methyl-2,6-heptadiene compound (1) having the leaving group X at position 1, wherein X is as defined above.

Another aspect of the present invention provides a 2-methyl-2,6-heptadiene compound of the following general formula (1') having X' at position 1:

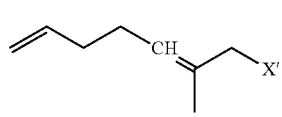

(1')

wherein X' represents an acyloxy group having 1 to 10 carbon atoms including the carbon atom of the carbonyl group.

Another aspect of the present invention provides a 2-methyl-2,6-heptadiene compound of the following general formula (1") having X" at position 1:

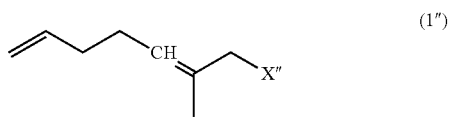

(1")

wherein X" represents an alkanesulfonyloxy group having 1 to 10 carbon atoms or an arenesulfonyloxy group having 6 to 20 carbon atoms.

The present invention provides a process for efficiently and industrially preparing 6-isopropenyl-3-methyl-9-decenyl acetate, without an oxidation reaction that is industrially unfavorable in view of safety, economy, and environmental burden. The present invention also provides a 2-methyl-2,6-heptadiene compound (1') and a 2-methyl-2,6-heptadiene compound (1"), which are useful intermediates in the preparation of 6-isopropenyl-3-methyl-9-decenyl acetate.

DETAILED DESCRIPTION OF THE PREFERRED EMBODIMENTS

Embodiments of the present invention will be explained hereinafter in detail. It should be understood that the present invention is not limited to or by the embodiments. In the intermediates, the reagents, and the target compounds represented by the chemical formulae in the present specification, there may be some stereoisomers such as enantiomers or diastereoisomers. Unless otherwise stated, each chemical formula shall be interpreted to represent all of these isomers. The isomer may be either alone or in combination thereof.

The present inventors have contemplated a plan for the synthesis of 6-isopropenyl-3-methyl-9-decenyl acetate (5), as described below.

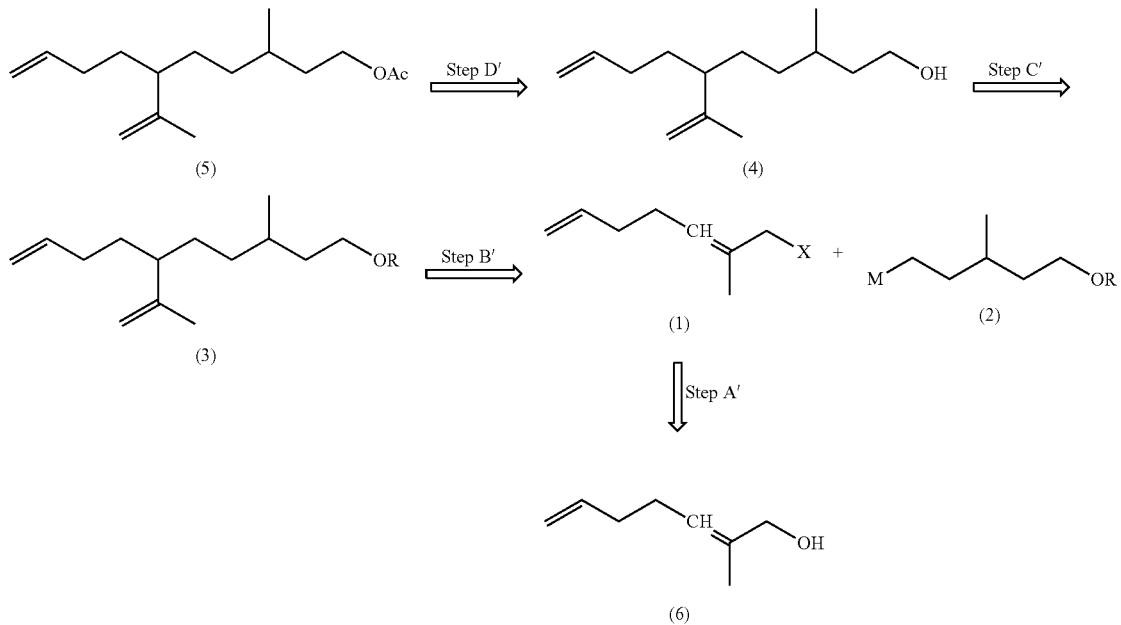

In reaction formulae of the retrosynthetic analysis shown above, the open arrows represent transforms in the retrosynthetic analysis. Ac represents an acetyl group; R represents a protecting group for a hydroxyl group; X represents an acyloxy group having 1 to 10 carbon atoms including the carbon atom of the carbonyl group, an alkanesulfonyloxy group having 1 to 10 carbon atoms, an arenesulfonyloxy group having 6 to 20 carbon atoms, or a halogen atom; M represents Li, $MgZ^1$, $ZnZ^1$, Cu, $CuZ^1$, or $CuLiZ^1$, wherein $Z^1$ represents a halogen atom or a $CH_2CH_2CH(CH_3)CH_2CH_2OR$ group; and R represents a protecting group for a hydroxyl group.

Step D'

A target compound of the present invention, 6-isopropenyl-3-methyl-9-decenyl acetate (5), is thought to be synthesized via acetylation of 6-isopropenyl-3-methyl-9-decenol (4).

The formula (5) represents (3R,6R)-6-isopropenyl-3-methyl-9-decenyl acetate of the following formula (5a), (3R,6S)-6-isopropenyl-3-methyl-9-decenyl acetate of the following formula (5b), (3 S,6R)-6-isopropenyl-3-methyl-9-decenyl acetate of the following formula (5c), or (3 S,6S)-6-isopropenyl-3-methyl-9-decenyl acetate of the following formula (5d), or a combination thereof.

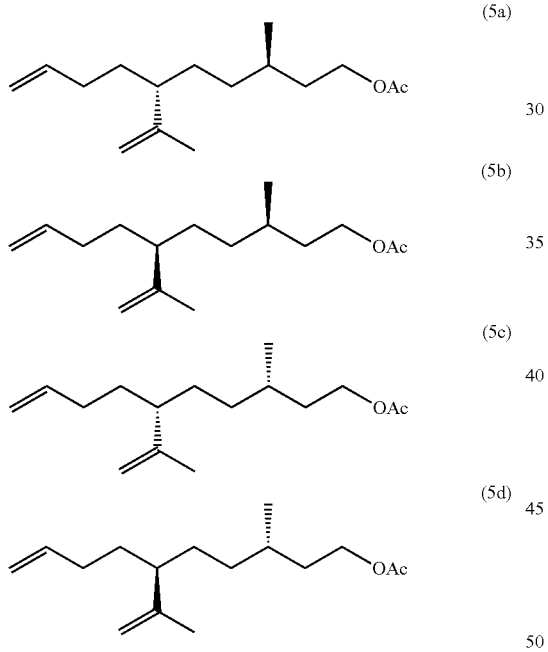

The formula (4) represents (3R,6R)-6-isopropenyl-3-methyl-9-decenol of the following formula (4a), (3R,6S)-6-isopropenyl-3-methyl-9-decenol of the following formula (4b), (3 S,6R)-6-isopropenyl-3-methyl-9-decenol of the following formula (4c), or (3S,6S)-6-isopropenyl-3-methyl-9-decenol of the following formula (4d), or a combination thereof.

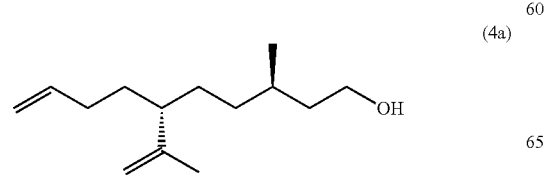

Step C'

A target compound, 6-isopropenyl-3-methyl-9-decenol (4), is thought to be synthesized via deprotection of the 6-isopropenyl-3-methyl-9-decene compound (3) having the protected hydroxyl group at position 1.

The general formula (3) represents a (3R,6R)-6-isopropenyl-3-methyl-9-decene compound of the following general formula (3a) having a protected hydroxyl group at position 1, a (3R,6S)-6-isopropenyl-3-methyl-9-decene compound of the following general formula (3b) having a protected hydroxyl group at position 1, a (3S,6R)-6-isopropenyl-3-methyl-9-decene compound of the following general formula (3c) having a protected hydroxyl group at position 1, or a (3S,6S)-6-isopropenyl-3-methyl-9-decene compound of the following general formula (3d) having a protected hydroxyl group at position 1, or a combination thereof.

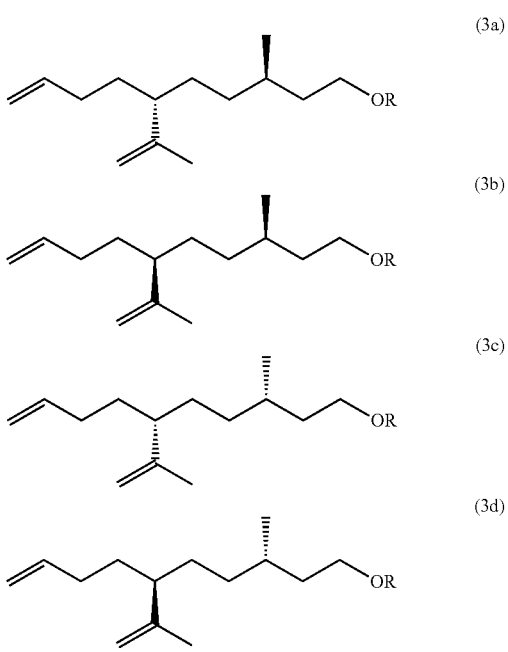

Step B'

A target compound, 6-isopropenyl-3-methyl-9-decene compound (3) having a protected hydroxyl group at position 1, is thought to be synthesized via a regioselective reaction between a 3-methylpentyl nucleophilic reagent (2) having a protected hydroxyl group at position 5 and the carbon atom at position 3 of a 2-methyl-2,6-heptadiene compound (1) having a leaving group X at position 1.

The general formula (2) represents a (R)-3-methylpentyl nucleophilic reagent of the following general formula (2a) having a protected hydroxyl group at position 5, or a (S)-3-methylpentyl nucleophilic reagent of the following general formula (2b) having a protected hydroxyl group at position 5, or a combination thereof. In the nomenclature of the nucleophilic reagents of the general formulae (2a) and (2b), M has a higher priority over O in the R/S system.

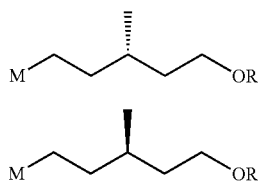

(2a)

(2b)

The general formula (1) represents a (Z)-2-methyl-2,6-heptadiene compound of the following general formula (1a) having a leaving group X at position 1, or an (E)-2-methyl-2,6-heptadiene compound of the following general formula (1b) having a leaving group X at position 1, or a combination thereof.

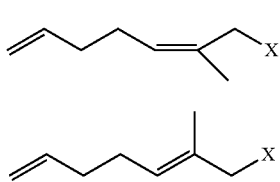

(1a)

(1b)

Step A'

A target compound, 2-methyl-2,6-heptadiene compound (1) having a leaving group X at position 1, is thought to be synthesized via a conversion of the hydroxyl group of 2-methyl-2,6-heptadienol (6).

The formula (6) represents (Z)-2-methyl-2,6-heptadienol of the following formula (6a), or (E)-2-methyl-2,6-heptadienol of the following formula (6b), or a combination thereof.

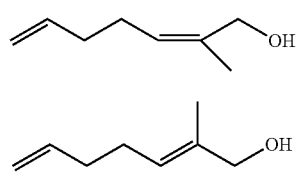

(6a)

(6b)

In consideration of the retrosynthetic analysis mentioned above, an embodiment of the present invention may be depicted by the following chemical reaction scheme.

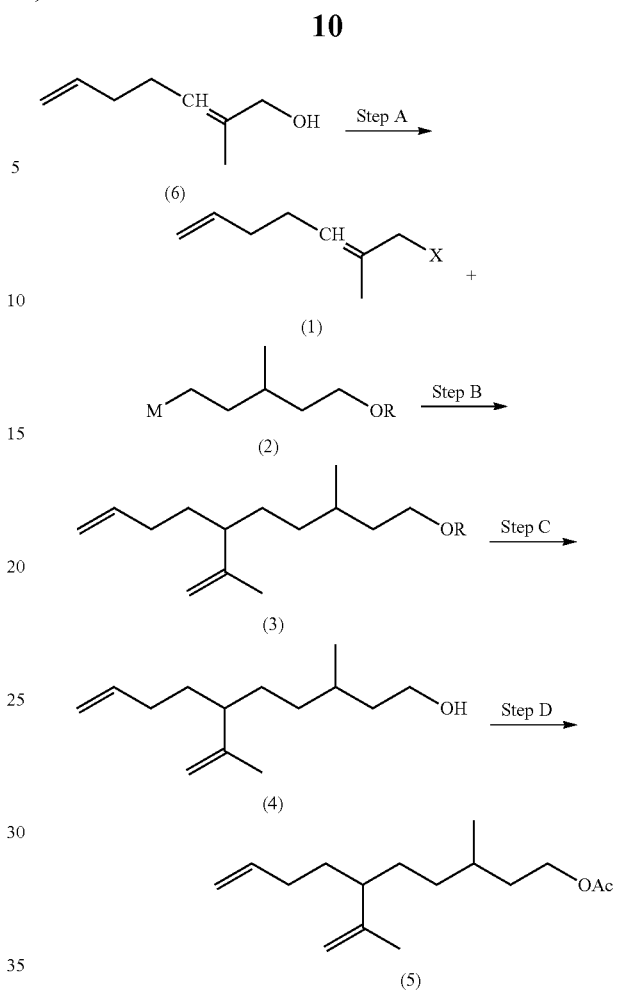

Thus, the chemical reaction scheme comprises step A in which a 2-methyl-2,6-heptadiene compound (1) having a leaving group X at position 1 is synthesized via conversion of the hydroxyl group of 2-methyl-2,6-heptadienol (6); step B in which a 6-isopropenyl-3-methyl-9-decene compound (3) having a protected hydroxyl group at position 1 is synthesized via a regioselective nucleophilic substitution reaction between the 3-methylpentyl nucleophilic reagent (2) having a protected hydroxyl group at position 5 and the carbon atom at position 3 of the 2-methyl-2,6-heptadiene compound (1) having a leaving group X at position 1; step C in which the 6-isopropenyl-3-methyl-9-decene compound (3) having a protected hydroxyl group at position 1 is deprotected; and finally step D in which a target compound of the present invention, 6-isopropenyl-3-methyl-9-decenyl acetate (5), is synthesized by acetylating 6-isopropenyl-3-methyl-9-decenol (4).

Steps A to D, which are embodiments of the present invention, will be described in detail below. These will be explained in the order of steps B, C, D and A. In the explanation of step B, useful intermediates, 2-methyl-2,6-heptadiene compound (1') and a 2-methyl-2,6-heptadiene compound (1"), will also be described.

[1] Step B

Step B to obtain a 6-isopropenyl-3-methyl-9-decene compound (3) having a protected hydroxyl group at position 1 will be described below. The 6-isopropenyl-3-methyl-9-decene compound (3) having a protected hydroxyl group at position 1 is synthesized by a nucleophilic substitution reaction between the 2-methyl-2,6-heptadiene compound (1) having a leaving group X at position 1 and the 3-methylpentyl nucleophilic reagent (2) having a protected hydroxyl group at position 5, as shown in the following chemical reaction formula.

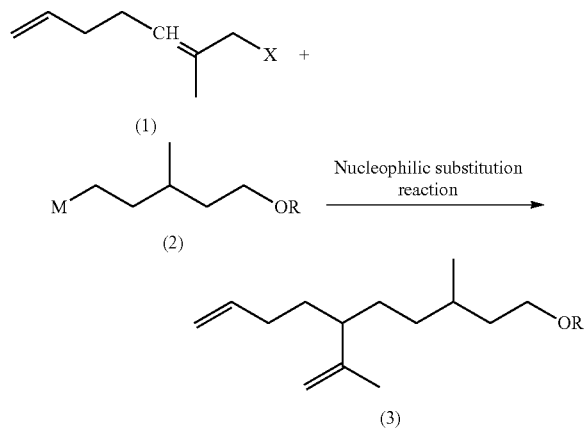

First, the 2-methyl-2,6-heptadiene compound of the following general formula (1) having a leaving group X at position 1 will be described.

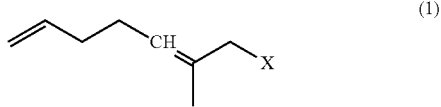

X in the general formula (1) represents a leaving group.

The 2-methyl-2,6-heptadiene compound (1) having a leaving group X at position 1 may be a (Z)-2-methyl-2,6-heptadiene compound of the following general formula (1a) having a leaving group X at position 1, or an (E)-2-methyl-2,6-heptadiene compound of the following general formula (1b) having a leaving group X at position 1. The 2-methyl-2,6-heptadiene compound (1) having a leaving group X at position 1 may be either isomer or a mixture of the isomers.

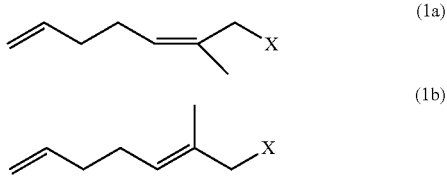

The leaving group X represents an acyloxy group having 1 to 10 carbon atoms including the carbon atom of the carbonyl group, an alkanesulfonyloxy group having 1 to 10 carbon atoms, an arenesulfonyloxy group having 6 to 20 carbon atoms, or a halogen atom and may be appropriately selected from these in view of the reactivity, reaction selectivity, availability of raw materials, easiness of synthesis, storage stability, toxicity, and/or price.

Examples of the acyloxy group having 1 to 10 carbon atoms including the carbon atom of the carbonyl group include linear aliphatic acyloxy groups such as a formyloxy group, an acetoxy group, a propanoyloxy group, a butanoyloxy group, a pentanoyloxy group, a hexanoyloxy group, a heptanoyloxy group, an octanoyloxy group, a nonanoyloxy group, a decanoyloxy group, and a crotonyloxy group; branched aliphatic acyloxy groups such as a 2-methylpropanoyloxy group, a pivaloyloxy group, a 2-methylbutanoyloxy group, a 3-methyl-2-butenoyloxy group, and a 3-methyl-3-butenoyloxy group; halogenated acyloxy groups such as a trichloroacetoxy group and a trifluoroacetoxy group; aromatic acyloxy groups such as a benzoyloxy group; and isomers thereof. A part of the hydrogen atoms in the acyloxy groups may be substituted with, for example, a methyl group, an ethyl group, or a halogen atom. Examples of the halogen atom include a chlorine atom, a bromine atom, and an iodine atom.

Among the acyloxy groups, a formyloxy group, an acetoxy group, a propanoyloxy group, a pivaloyloxy group, a 2-methylpropanoyloxy group, and a benzoyloxy group are preferred in view of the availability.

Examples of the alkanesulfonyloxy group having 1 to 10 carbon atoms include a methanesulfonyloxy group, an ethanesulfonyloxy group, a 1-butanesulfonyloxy group, a 1-pentanesulfonyloxy group, a 1-hexanesulfonyloxy group, a 1-heptanesulfonyloxy group, a 1-octanesulfonyloxy group, a 1-nonanesulfonyloxy group, a 1-decanesulfonyloxy group, an allylsulfonyloxy group, a 10-camphorsulfonyloxy group, a trifluoromethanesulfonyloxy group, an α-benzylsulfonyloxy group, and isomers thereof. A part of the hydrogen atoms in the alkanesulfonyloxy groups may be substituted with, for example, a methyl group, an ethyl group, or a halogen atom. Examples of the halogen atom include a chlorine atom, a bromine atom, and an iodine atom.

Among the alkanesulfonyloxy groups, a methanesulfonyloxy group and an ethanesulfonyloxy group are preferred in view of the availability.

Examples of the arenesulfonyloxy group having 6 to 20 carbon atoms include a benzenesulfonyloxy group, a 4-chlorobenzenesulfonyloxy group, a 4-methoxybenzenesulfonyloxy group, a 2-nitrobenzensulfonyloxy group, a 2,4,6-trimethylbenzenesulfonyloxy group, a p-toluenesulfonyloxy group, a 1-naphthalenesulfonyloxy group, a 2-naphthalenesulfonyloxy group, and isomers thereof. A part of the hydrogen atoms in the arenesulfonyloxy groups may be substituted with, for example, a methyl group, an ethyl group, or a halogen atom. Examples of the halogen atom include a chlorine atom, a bromine atom, and an iodine atom.

Among the arenesulfonyloxy groups, a benzenesulfonyloxy group and a p-toluenesulfonyloxy group are preferred in view of the availability.

Examples of the halogen atom include a fluorine atom, a chlorine atom, a bromine atom, and an iodine atom.

Among the halogen atoms, a chlorine atom and a bromine atom are preferred in view of the availability.

The 2-methyl-2,6-heptadiene compound (1) having a leaving group X at position 1 is particularly preferably a 2-methyl-2,6-heptadiene compound of the following general formula (1'):

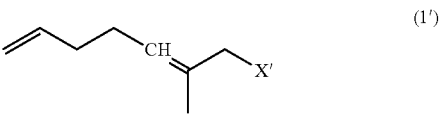

in view of the reactivity and/or economy.

X' in the general formula (1') represents an acyloxy group having 1 to 10 carbon atoms including the carbon atom of the carbonyl group.

Specific examples of the acyloxy group having 1 to 10 carbon atoms including the carbon atom of the carbonyl group are same as those mentioned for the acyloxy group as the leaving group X.

Besides the 2-methyl-2,6-heptadiene compound (1'), is preferred a 2-methyl-2,6-heptadiene compound of the following general formula (1"):

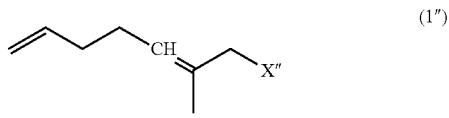

(1")

in view of the availability of raw materials.

X" in the general formula (1") represents an alkanesulfonyloxy group having 1 to 10 carbon atoms or an arenesulfonyloxy group having 6 to 20 carbon atoms.

Specific examples of the alkanesulfonyloxy group having 1 to 10 carbon atoms and the arenesulfonyloxy group having 6 to 20 carbon atoms are those mentioned for the 3) CH leaving group X.

The leaving group X is at the allyl position in the 2-methyl-2,6-heptadiene compound (1) having a leaving group X at position 1. Therefore, the 3-methylpentyl nucleophilic reagent (2) having a protected hydroxyl group at position 5, may attack the carbon atom at position 1 to which the leaving group X is attached and the carbon atom at position 3 in the 2-methyl-2,6-heptadiene compound (1) having a leaving group X at position 1.

When the 3-methylpentyl nucleophilic reagent (2) having a protected hydroxyl group at position 5, attacks the carbon atom at position 3 of the 2-methyl-2,6-heptadiene compound (1) having a leaving group X at position 1 (so called $S_N2'$ mechanism), a nucleophilic substitution occurs together with allylic rearrangement to produce a 6-isopropenyl-3-methyl-9-decene compound (3) having a protected hydroxyl group at position 1.

Meanwhile, when the 3-methylpentyl nucleophilic reagent (2) having a protected hydroxyl group at position 5, attacks the carbon atom at position 1 of the 2-methyl-2,6-heptadiene compound (1) having a leaving group X at position 1 (so called $S_N2$ mechanism), a 3,7-dimethyl-7,11-dodecadiene compound of the following general formula (3') having a protected hydroxyl group at position 1 is produced.

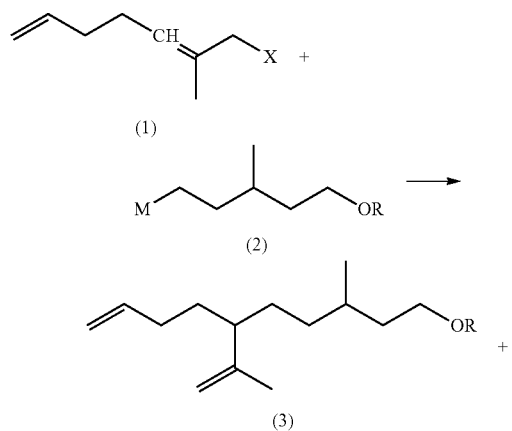

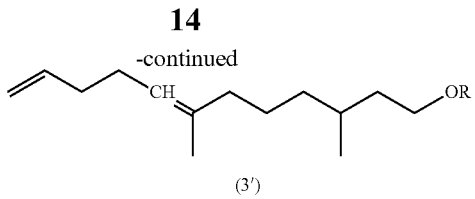

(3')

That is, the production of the 6-isopropenyl-3-methyl-9-decene compound (3) having a protected hydroxyl group at position 1 may compete with the production of the 3,7-dimethyl-7,11-dodecadiene compound (3') in step B. Among the nucleophilic substitution reaction conditions described below, optimal conditions might be adopted to reduce the production of the by-product, 3,7-dimethyl-7,11-dodecadiene compound (3') having a protected hydroxyl group at position 1, and to enhance the production of the 6-isopropenyl-3-methyl-9-decene compound (3) having a protected hydroxyl group at position 1. Examples of the optimal conditions include the use of the 2-methyl-2,6-heptadiene compound (1') in which the leaving group X in the 2-methyl-2,6-heptadiene compound (1) having a leaving group X at position 1 is an acyloxy group having 1 to 10 carbon atoms including the carbon atom of the carbonyl group, the use of the 5-(1-ethoxyethyloxy)-3-methylpentylmagnesium halide nucleophilic reagent in which the protecting group is a 1-ethoxyethyl group, and the use of a combinational catalyst of a copper (including cupric and cuprous) halide and a lithium salt in the nucleophilic substitution reaction. The catalyst combination is thought to suppress the formation of the by-product and increase a yield of the target compound (for example, see Examples 6 and 7 below).

The 3-methylpentyl nucleophilic reagent (2) having a protected hydroxyl group at position 5 may be a (R)-3-methylpentyl nucleophilic reagent of the following general formula (2a) having a protected hydroxyl group at position 5, or a (S)-3-methylpentyl nucleophilic reagent of the following general formula (2b) having a protected hydroxyl group at position 5, where M has a higher priority over O in the R/S system. The 3-methylpentyl nucleophilic reagent (2) may be either isomer or a combination of the isomers, but preferably contains the compound (2a) having the same backbone as a naturally occurred sex pheromone borne by female California red scale.

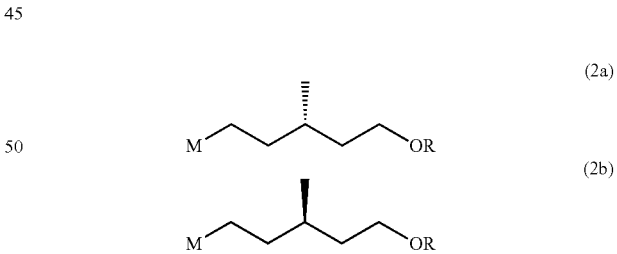

The 6-isopropenyl-3-methyl-9-decene compound (3) having a protected hydroxyl group at position 1 may be a (3R,6R)-6-isopropenyl-3-methyl-9-decene compound of the following general formula (3a) having a protected hydroxyl group at position 1, a (3R,6S)-6-isopropenyl-3-methyl-9-decene compound of the following general formula (3b) having a protected hydroxyl group at position 1, a (3S,6R)-6-isopropenyl-3-methyl-9-decene compound of the following general formula (3c) having a protected hydroxyl group at position 1, or a (3S,6S)-6-isopropenyl-3-methyl-9-decene compound of the following general formula (3d) having a protected hydroxyl group at position 1. The 6-isopropenyl- 3-methyl-9-decene compound (3) may be either isomer or a mixture of the isomers, but preferably contains the compound (3c) having the same backbone as a naturally occurred sex pheromone borne by female California red scale.

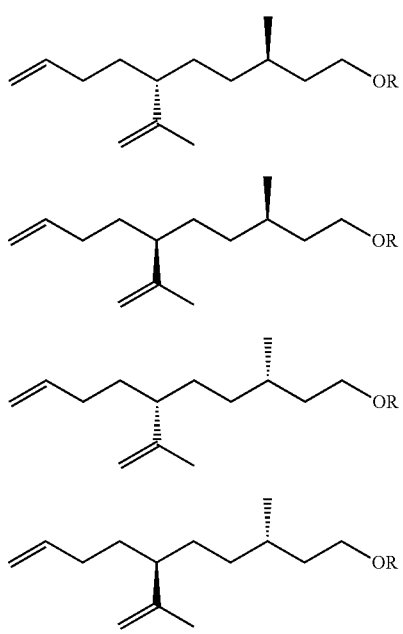

The 3,7-dimethyl-7,11-dodecadiene compound (3') having a protected hydroxyl group at position 1, which is by-produced in the nucleophilic substitution reaction, may be an (R,Z)-3,7-dimethyl-7,11-dodecadiene compound of the following general formula (3'a), having a protected hydroxyl group at position 1 an (R,E)-3,7-dimethyl-7,11-dodecadiene compound of the following general formula (3'b) having a protected hydroxyl group at position 1, an (S,Z)-3,7-dimethyl-7,11-dodecadiene compound of the following general formula (3'c) having a protected hydroxyl group at position 1, an (S,E)-3,7-dimethyl-7,11-dodecadiene compound of the following general formula (3'd) having a protected hydroxyl group at position 1, or a mixture thereof.

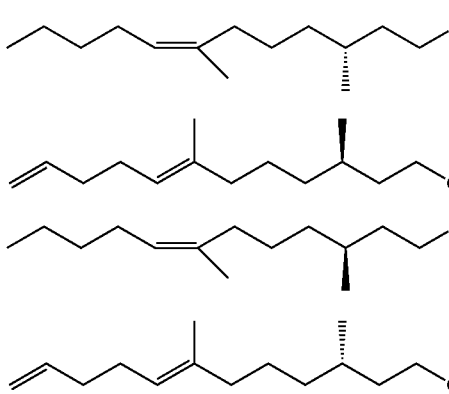

R in the 3-methylpentyl nucleophilic reagent (2) having a protected hydroxyl group at position 5 represents a protecting group for a hydroxyl group. The protecting group may be appropriately selected from known protecting groups for hydroxyl groups that are stable during reactions, post-treatments, and storage and are easily deprotected. Examples of the appropriate protecting group R include oxyalkyl groups such as a methoxymethyl group, a 2-methoxyethoxymethyl group, a benzyloxymethyl group, a p-methoxybenzyloxymethyl group, a 2,2,2-trichloroethoxymethyl group, a 1-ethoxyethyl group, and a tetrahydropyranyl group, and isomers thereof. A part of the hydrogen atoms in the protecting groups may be substituted with, for example, a methyl group or an ethyl group. Examples of other protecting groups include trialkylsilyl groups such as a trimethylsilyl group, a triethylsilyl group, a triisopropylsilyl group, and a t-butyldimethylsilyl group; monoalkyldiarylsilyl groups such as a t-butyldiphenylsilyl group; and isomers thereof. A part of the hydrogen atoms in the silyl groups may be substituted with, for example, a methyl group, an ethyl group, or a halogen atom. Examples of the halogen atom include a chlorine atom, a bromine atom, and an iodine atom.

The protecting group R is preferably a tetrahydropyranyl group or a 1-ethoxyethyl group in view of the reactivity and/or economy.

M in the 3-methylpentyl nucleophilic reagent (2) having a protected hydroxyl group at position 5 represents Li, $MgZ^1$, $ZnZ^1$, Cu, $CuZ^1$, or $CuLiZ^1$, wherein $Z^1$ represents a halogen atom or a $CH_2CH_2CH(CH_3)CH_2CH_2OR$ group, and R represents a protecting group for a hydroxyl group.

The 3-methylpentyl nucleophilic reagent (2) having a protected hydroxyl group at position 5 is preferably an organolithium reagent such as a 3-methylpentyl lithium compound having a protected hydroxyl group at position 5 or an organomagnesium reagent such as a 3-methylpentylmagnesium halide compound (Grignard reagent) having a protected hydroxyl group at position 5 in view of the reactivity, selectivity, and/or easiness of preparation. In particular, a 3-methylpentylmagnesium halide compound (Grignard reagent) is preferred.

Specific examples of the 3-methylpentylmagnesium halide compound having a protected hydroxyl group at position 5 include a 3-methylpentylmagnesium chloride compound having a protected hydroxyl group at position 5, a 3-methylpentylmagnesium bromide compound having a protected hydroxyl group at position 5, and a 3-methylpentylmagnesium iodide compound having a protected hydroxyl group at position 5.

The 3-methylpentyl nucleophilic reagent (2) having a protected hydroxyl group at position 5, may be prepared in a conventional method from, for example, its corresponding halide, 3-methylpentyl halide compound having a protected hydroxyl group at position 5. Examples of the 3-methylpentyl halide compound having a protected hydroxyl group at position 5 include a 3-methylpentyl chloride compound having a protected hydroxyl group at position 5, a 3-methylpentyl bromide compound having a protected hydroxyl group at position 5, and a 3-methylpentyl iodide compound having a protected hydroxyl group at position 5. In view of the easiness of preparation and/or stability of the 3-methylpentyl nucleophilic reagent (2) having a protected hydroxyl group at position 5, preferred are a 3-methyl-pentyl chloride compound having a protected hydroxyl group at position 5 and a 3-methyl-pentyl bromide compound having a protected hydroxyl group at position 5.

The 3-methylpentyl nucleophilic reagent (2) having a protected hydroxyl group at position 5, may be prepared by subjecting an organolithium reagent or an organomagnesium reagent to a metal exchange reaction with a stoichiometric amount (1 mol) of a transition metal compound or may be formed in situ by reacting an organolithium reagent or a Grignard reagent with a very small amount, such as 0.0001 or more, of a transition metal compound.

Examples of the transition metal compound include those comprising copper, iron, nickel, palladium, zinc, titanium, or silver. Preferred are cuprous halides such as copper(I) chloride, copper(I) bromide, and copper(I) iodide; cupric halides such as copper(II) chloride, copper(II) bromide, and copper (II) iodide; copper cyanides such as copper(I) cyanide and copper(II) cyanide; copper oxides such as copper(I) oxide and copper(II) oxide; and copper compounds such as dilithium tetrachlorocuprate ($Li_2CuCl_4$). Cuprous halides are particularly preferred in view of the reactivity.

An amount of the transition metal compound may be from a very small amount, such as from 0.0001 to 1-time a stoichiometric amount relative to the amount of the 2-isopropenyl-5-hexenyl compound comprising a metal element of Group I or II, or even a 100-times excessive amount. An amount of 0.0001 to 10 mol is preferred.

R in the 6-isopropenyl-3-methyl-9-decene compound (3) having a protected hydroxyl group at position 1 is as defined for the general formula (2).

In the nucleophilic substitution reaction between the 2-methyl-2,6-heptadiene compound (1) having a leaving group X at position 1 and the 3-methylpentyl nucleophilic reagent (2) having a protected hydroxyl group at position 5, an organometallic reagent comprising a metal element of the Group I or II or a transition metal element is typically used.

When the transition metal compound is used in the nucleophilic substitution reaction, a phosphorus compound may also be used in view of enhancement of solubility of the transition metal compound in a solvent Examples of the phosphorus compounds include trialkyl phosphites such as triethyl phosphite; and triarylphosphine such as triphenylphosphine.

The phosphorus compound may be used alone or in combination thereof, if necessary. The phosphorus compound may be commercially available one.

An amount of the phosphorus compound used is from 0.001 to 1000 parts per 100 parts of the transition metal compound to improve the solubility of the transition metal compound in a solvent.

In the nucleophilic substitution reaction, 0.001 to 1,000 mol of a lithium salt such as lithium chloride, lithium bromide, or lithium iodide per mol of the 2-methyl-2,6-heptadiene compound (1) having a leaving group X at position 1 may be used as a catalyst for the reaction.

In the nucleophilic substitution reaction, a combination of the cuprous halide and the lithium salt is particularly preferred in view of the reactivity including a production ratio of a target compound to a byproduct (see Examples 6 and 7 below).

An amount of the 3-methylpentyl nucleophilic reagent (2) having a protected hydroxyl group at position 5 may be arbitrarily set in view of the reagent, reaction conditions, a reaction yield, economy such as prices of intermediates, and/or easiness of purification of the target compound from a reaction mixture, and is preferably from 0.2 to 100 mol, more preferably from 0.5 to 20 mol, and even more preferably from 0.8 to 5 mol, per mol of the 2-methyl-2,6-heptadiene compound (1).

The nucleophilic substitution reaction is carried out in the presence of a solvent and, if necessary, under heating or cooling.

Examples of the solvent used in the nucleophilic substitution reaction include ethers such as diethyl ether, di-n-butyl ether, t-butyl methyl ether, cyclopentyl methyl ether, tetrahydrofuran, and 1,4-dioxane; hydrocarbons such as hexane, heptane, benzene, toluene, xylene, and cumene; and aprotic polar solvents such as N,N-dimethylformamide (DMF), N,N-dimethylacetamide, N,N-dimethylpropionamide, 1,3-dimethyl-2-imidazolidinone (DMI), dimethyl sulfoxide (DMSO), and hexamethylphosphoric triamide (HMPA). Ethers are preferred in view of the reactivity. The solvent may be the ether alone or, if necessary, a combination of the ether and one or more of the aforesaid solvents except the ethers. The solvent may be commercially available one.

An amount of the solvent used is not particularly limited and is preferably from 10 to 1,000,000 g, more preferably from 100 to 100,000 g, and even more preferably from 150 to 10,000 g, per mol of the 3-methylpentyl nucleophilic reagent (2) having a protected hydroxyl group at position 5.

A reaction temperature of the nucleophilic substitution reaction is preferably from −78° C. to a boiling point of the solvent, more preferably from −78 to 100° C.

A reaction time of the nucleophilic substitution reaction may be arbitrarily set and may be optimized by monitoring the reaction progress with gas chromatography (GC) or thin layer chromatography (TLC). The reaction time is typically and preferably from 5 minutes to 240 hours.

When the 6-isopropenyl-3-methyl-9-decene compound (3) having a protected hydroxyl group at position 1 obtained in the nucleophilic substitution reaction has a sufficient purity, the 6-isopropenyl-3-methyl-9-decene compound (3) may be used as such in a subsequent step. Alternatively, the crude product may be purified in any purification method used in usual organic synthesis, such as distillation or various chromatography. Distillation is particularly preferred in view of the industrial economy.

[2] Step C

Step C to obtain 6-isopropenyl-3-methyl-9-decenol (4) will be described below. 6-Isopropenyl-3-methyl-9-decenol (4) is synthesized by subjecting the 6-isopropenyl-3-methyl-9-decene compound (3) having a protected hydroxyl group at position 1 obtained in step B to a deprotection reaction, as shown in the following chemical reaction formula.

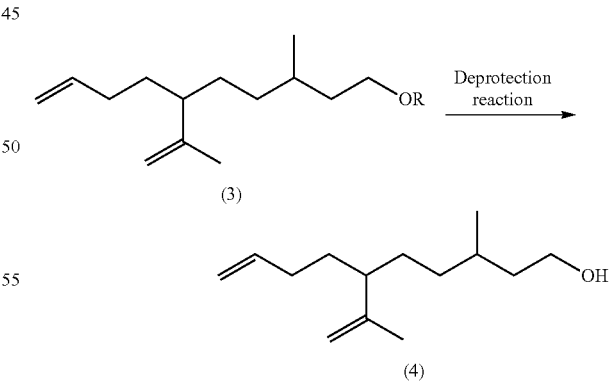

In the deprotection reaction, an isomer may be by-produced, the isopropenyl group in the 6-isopropenyl-3-methyl-9-decene compound (3) having a protected hydroxyl group at position 1 is converted into a 1-methyl ethylidene group in the isomer of the following formula (4') with the converted double bond at the position 4 which was originated from the double bond in the aforesaid isopropenyl group.

Among the deprotection reaction conditions described below, optimal conditions might be adopted to reduce the formation of the by-produced isomer (4') and to enhance the formation of 6-isopropenyl-3-methyl-9-decenol (4). Examples of the optimal conditions include use of the 6-isopropenyl-3-methyl-9-decene compound (3) in which R is a 1-ethoxyethyl group, incorporation of acetic acid and water in the deprotection reaction and a reaction temperature of 120° C. or below.

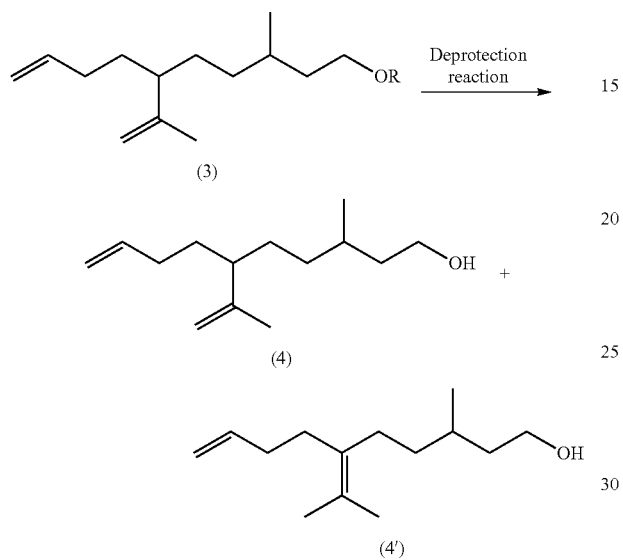

The 6-isopropenyl-3-methyl-9-decene compound (4) may be (3R,6R)-6-isopropenyl-3-methyl-9-decenol of the following formula (4a), (3R,6S)-6-isopropenyl-3-methyl-9-decenol of the following formula (4b), (3S,6R)-6-isopropenyl-3-methyl-9-decenol of the following formula (4c), or (3S,6S)-6-isopropenyl-3-methyl-9-decenol of the following formula (4d). The 6-isopropenyl-3-methyl-9-decene compound (4) may be either isomer or a combination of the isomers, but preferably contains the compound (4c) having the same backbone as a naturally occurred sex pheromone borne by female California red scale.

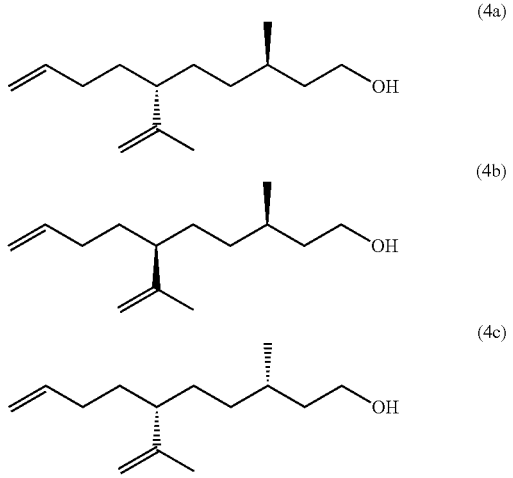

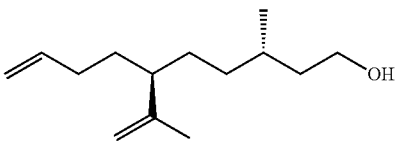

The isomer (4') represents an (R)-isomer (4') of the following formula (4'a), an (S)-isomer (4') of the following formula (4'b), or a combination thereof.

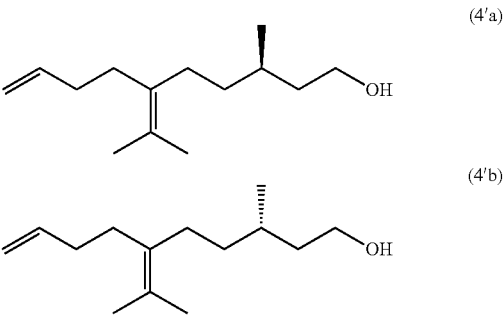

Deprotection reaction conditions may be appropriately selected, depending upon a type of the protecting group in the 6-isopropenyl-3-methyl-9-decene compound (3) having a protected hydroxyl group at position 1. For example, when the protecting group is an oxyalkyl group such as a methoxymethyl group, a deprotection reaction by solvolysis with an acid may be conducted. When the protecting group is a silyl group such as a t-butyldimethylsilyl group, a deprotection reaction with a fluoride ion may be conducted, besides the deprotection reaction by solvolysis with an acid.

For the deprotection reaction with an acid, 6-isopropenyl-3-methyl-9-decenol (4) is obtained by adding an acid and, if necessary, water or a solvent to the 6-isopropenyl-3-methyl-9-decene compound (3) having a protected hydroxyl group at position 1, followed by cooling or heating.

Examples of the acid used in the deprotection reaction include inorganic acids such as hydrochloric acid, hydrobromic acid, hydroiodic acid, sulfuric acid, nitric acid, and phosphoric acid, or salts thereof; organic acids such formic acid, acetic acid, propionic acid, oxalic acid, trifluoroacetic acid, methanesulfonic acid, benzenesulfonic acid, p-toluenesulfonic acid (p-TsOH), and naphthalenesulfonic acid, or salts thereof; Lewis acids such as lithium tetrafluoroborate, boron trifluoride, boron trichloride, boron tribromide, aluminum trichloride, zinc chloride, zinc bromide, zinc iodide, tin tetrachloride, tin tetrabromide, tin dichloride, titanium tetrachloride, titanium tetrabromide, and trimethylsilyl iodide; oxides such as alumina, silica gel, and titania; and minerals such as montmorillonite.

The acid used in the deprotection reaction is preferably acetic acid in view of the economy, reactivity, and/or suppression of formation of the byproduct, the isomer (4').

The acid may be used alone or in combination thereof, if necessary. The acid may be commercially available one.

An amount of the acid is preferably small in view of the economy and may be arbitrarily set as long as a practically sufficient reaction rate is achieved. The amount of the acid is preferably from 0.00001 to 10,000 mol, more preferably from 0.0001 to 1,000 mol, and even more preferably from 0.001 to 100 mol, per mol of the 6-isopropenyl-3-methyl-9-decene compound (3) having a protected hydroxyl group at position 1.

When water is additionally used in the deprotection reaction with the acid, an amount of the water is preferably from 1 to 10,000 mol, more preferably from 1 to 1,000 mol, and even more preferably from 1 to 500 mol, per mol of the 6-isopropenyl-3-methyl-9-decene compound (3) having a protected hydroxyl group at position 1.

Examples of the solvent used in the deprotection reaction with an acid include ethers such as diethyl ether, dibutyl ether, tetrahydrofuran, and 1,4-dioxane; hydrocarbons such as hexane, heptane, benzene, toluene, xylene, and cumene; chlorinated solvents such as methylene chloride, chloroform, and trichloroethylene; ketones such as acetone and methyl ethyl ketone; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); nitriles such as acetonitrile and propionitrile; esters such as ethyl acetate and n-butyl acetate; and alcohols such as methanol, ethanol, and t-butyl alcohol.

The solvent may be used alone or in combination thereof, if necessary. The solvent may be commercially available one.

When water or an alcohol is used as the solvent in the deprotection, a compound having the alcohol might form a by-product adduct to the double bond of 6-isopropenyl-3-methyl-9-decenol (4) and/or the isomer (4'). This side reaction can be suppressed by adopting appropriate conditions such as an acid and/or reaction temperature. Examples of the appropriate conditions include the use of acetic acid and/or a reaction temperature of 120° C. or lower.

An amount of the solvent used in the deprotection reaction with an acid is preferably from 10 g to 10,000 g, per mol of the 6-isopropenyl-3-methyl-9-decene compound (3) having a protected hydroxyl group at position 1.

A reaction temperature of the deprotection reaction with an acid varies, depending on reaction conditions, and is preferably from −78 to 160° C., more preferably from −50 to 140° C., and even more preferably from −30 to 120° C.

A reaction time of the deprotection reaction with an acid may be arbitrarily set. In view of the yield, it is desirable to monitor the reaction with gas chromatography (GC) or thin layer chromatography (TLC) to complete the reaction. The reaction time is typically from about 0.5 to 24 hours.

When the protecting group is a silyl group, and a deprotection reaction is conducted with fluoride ions, 6-isopropenyl-3-methyl-9-decenol (4) may be obtained by adding a reagent that can work as a fluoride ion source and, if necessary, a solvent to 6-isopropenyl-3-methyl-9-decene compound (3) having a protected hydroxyl group at position 1, and cooling or heating it. This deprotection reaction may also be carried out in combination with the acid mentioned for the deprotection reaction with an acid.

Examples of the reagent that can work as a fluoride ion source include inorganic acids such as hydrofluoric acid; amine complexes such as pyridine-nHF and triethylamine-nHF; inorganic salts such as cesium fluoride, potassium fluoride, lithium borofluoride (LiBF4), and ammonium fluoride; and organic salts such as tetrabutylammonium fluoride (TBAF).

The reagent that can work as a fluoride ion source may be used alone or in combination thereof, if necessary. The reagent that can work as a fluoride ion source may be commercially available one.

An amount of the reagent in the deprotection reaction with fluoride ions is preferably from 0.1 to 500 mol, more preferably from 0.1 to 50 mol, per mol of the 6-isopropenyl-3-methyl-9-decene compound (3) having a protected hydroxyl group at position 1.

A solvent, an amount of the solvent, a reaction time, and a reaction temperature in the deprotection reaction with fluoride ions are same as those mentioned for the deprotection reaction of 6-isopropenyl-3-methyl-9-decene compound (3) having a protected hydroxyl group at position 1 with an acid.

An alcohol compound might be by-produced in the deprotection reaction. For example, when a 1-ethoxyethoxy group is a protecting group and removed, ethanol is by-produced. When an alcohol compound is by-produced, the deprotection reaction may be carried out while removing the by-produced alcohol compound from the reaction system, for instance, by distillation.

When 6-isopropenyl-3-methyl-9-decenol (4) obtained from the deprotection reaction has a sufficient purity, it may be used as such in a subsequent step. Alternatively, the crude product may be purified in any purification method used in usual organic synthesis, such as distillation or various chromatography. Distillation is particularly preferred in view of the industrial economy.

[3] Step D

Step D to obtain 6-isopropenyl-3-methyl-9-decenyl acetate (5) will be described below. 6-Isopropenyl-3-methyl-9-decenyl acetate (5) is obtained by acetylating 6-isopropenyl-3-methyl-9-decenol (4) obtained in Step C, as shown in the following chemical reaction formula.

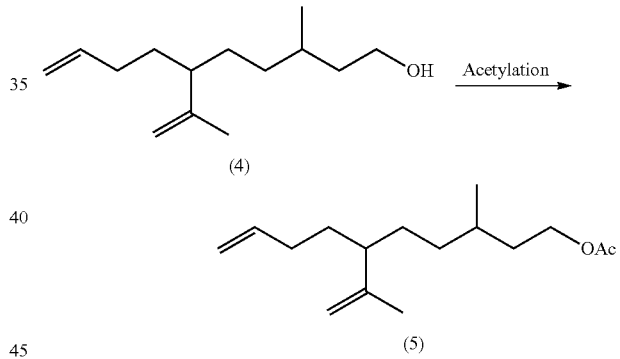

6-Isopropenyl-3-methyl-9-decenyl acetate (5) may be (3R,6R)-6-isopropenyl-3-methyl-9-decenyl acetate of the following formula (5a), (3R,6S)-6-isopropenyl-3-methyl-9-decenyl acetate of the following formula (5b), (3S,6R)-6-isopropenyl-3-methyl-9-decenyl acetate of the following formula (5c), or (3S,6S)-6-isopropenyl-3-methyl-9-decenyl acetate of the following formula (5d). 6-Isopropenyl-3-methyl-9-decenyl acetate (5) may be either isomer or a combination of the isomers, but preferably contains the compound (5c) having the same backbone as a naturally occurred sex pheromone borne by female California red scale.

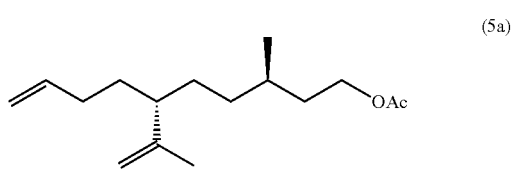

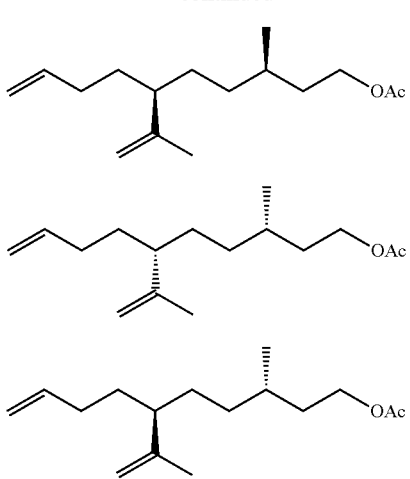

The acetylation may be done in any known manner for preparing an acetate ester, for example, (i) a reaction with an acetylating agent, (ii) a dehydration reaction with acetic acid, (iii) a transesterification with an acetate ester, and (iv) a conversion of 6-isopropenyl-3-methyl-9-decenol (4) into an alkylating agent, followed by acetoxylation with acetic acid or the like.

(i) Reaction with an acetylating Agent

The reaction with an acetylating agent may be carried out in a method of reacting 6-isopropenyl-3-methyl-9-decenol (4) with an acetylating agent and with a base in this order or in the reversed order, or simultaneously, in a single solvent or a mixed solvent, or in a method of reacting 6-isopropenyl-3-methyl-9-decenol (4) with an acetylating agent in the presence of a catalyst in a single solvent or a mixed solvent.

Examples of the acetylating agent include acetic chloride, acetic bromide, and acetic anhydride.

An amount of the acetylating agent used is preferably from 1 mol to 500 mol, more preferably from 1 mol to 50 mol, and even more preferably from 1 to 5 mol, per mol of 6-isopropenyl-3-methyl-9-decenol (4) in view of the economy.

Examples of the base used in the reaction with an acetylating agent include amines such as triethylamine, pyridine, N,N-dimethylaminopyridine, and N,N-dimethylaniline; organolithium compounds such as n-butyllithium, methyllithium, and phenyllithium; metal hydroxides such as sodium hydroxide and potassium hydroxide; and metal carbonates such as potassium carbonate, sodium carbonate, and sodium bicarbonate.

An amount of the base used is preferably from 1 to 500 mol, per mol of 6-isopropenyl-3-methyl-9-decenol (4).

A catalyst may be used when the acetylating agent is acetic anhydride. Examples of the catalyst include inorganic acids such as hydrochloric acid, hydrobromic acid, nitric acid, and sulfuric acid; organic acids such as trichloroacetic acid, trifluoroacetic acid, methanesulfonic acid, benzenesulfonic acid, and p-toluenesulfonic acid; Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide; and metal acetate salts such as sodium acetate and potassium acetate.

An amount of the catalyst used in the reaction with an acetylating agent is preferably from 0.0001 to 100 mol, per mol of 6-isopropenyl-3-methyl-9-decenol (4).

Examples of the solvent used in the reaction with an acetylating agent include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; ester solvents such as ethyl acetate and butyl acetate; and aprotic polar solvents such as N,N-dimethylformamide, N,N-dimethylacetamide, dimethyl sulfoxide, and hexamethylphosphoric triamide.

The solvent may be used alone or in combination thereof, if necessary. Depending on an acetylating agent to be used, the reaction can be carried out without a solvent. The solvent may be commercially available one.

An amount of the solvent used is preferably from 0 to 2000 g, more preferably from 0 to 500 g, per mol of 6-isopropenyl-3-methyl-9-decenol (4) in view of the economy.

A reaction temperature of the reaction with an acetylating agent is preferably from −50° C. to a boiling point of the solvent, more preferably from −30 to 80° C. in terms of the reactivity and yield.

A reaction time of the reaction with an acetylating agent may be arbitrarily set and may be optimized by monitoring the reaction progress with gas chromatography (GC) or thin layer chromatography (TLC). The reaction time is typically and preferably from 5 minutes to 240 hours.

(ii) Dehydration Reaction with acetic Acid

The dehydration reaction of 6-isopropenyl-3-methyl-9-decenol (4) with acetic acid may be carried out typically in the presence of an acid or Lewis acid catalyst.

Examples of the catalyst used in the dehydration reaction include inorganic acids such as hydrochloric acid, hydrobromic acid, nitric acid, and sulfuric acid; organic acids such as trichloroacetic acid, trifluoroacetic acid, methanesulfonic acid, benzenesulfonic acid, and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide.

The acid may be used alone or in combination thereof, if necessary. The acid may be commercially available one.

An amount of the catalyst used in the dehydration reaction is preferably from 0.001 to 1 mol, more preferably from 0.01 mol to 0.1 mol, per mol of 6-isopropenyl-3-methyl-9-decenol (4) in view of the economy and reactivity.

The dehydration reaction with acetic acid may be carried out, while removing water by-produced in the reaction, for example, by azeotropically distilling off the solvent and water at normal pressure or at a reduced pressure or by adding a dehydrating agent such as anhydrous magnesium sulfate, a molecular sieve, or dicyclohexylcarbodiimide into the reaction system.

Examples of the solvent used in the dehydration reaction include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; and ester solvents such as ethyl acetate and butyl acetate.

The solvent may be used alone or in combination thereof, if necessary. Depending on a reaction condition to be used, the dehydration reaction can be carried out without a solvent. The solvent may be commercially available one.

An amount of the solvent used in the dehydration reaction is preferably from 0 to 2000 g, more preferably from 0 to 500 g, per mol of 6-isopropenyl-3-methyl-9-decenol (4) in view of the economy.

A reaction temperature of the dehydration reaction may be appropriately selected, depending on a catalyst to be used. Typically, the reaction temperature is preferably from −50 to 200° C., more preferably from −20 to 100° C. in view of the reactivity and yield. When water by-produced in the reaction is removed by azeotropically distilling off water and the solvent, the reaction temperature is preferably an azeotropic boiling point or above at normal pressure or at a reduced pressure.

A reaction time of the dehydration reaction may be arbitrarily set and may be optimized by monitoring the reaction progress with gas chromatography (GC) or thin layer chromatography (TLC). The reaction time is typically and preferably from 5 minutes to 240 hours.

(iii) Transesterification with an acetate ester

The transesterification with an acetate ester is carried out typically in the presence of a catalyst and can be facilitated by removing an alcohol formed from the acetate ester at normal pressure or a reduced pressure.

Examples of the acetate ester used in the transesterification include acetate esters such as methyl acetate, ethyl acetate, propyl acetate, butyl acetate, and phenyl acetate. Among these acetate esters, methyl acetate and ethyl acetate are preferred in view of the economy, the reactivity, and easiness of removal of an alcohol formed from the acetate ester.

An amount of the acetate ester used in the transesterification is preferably from 1 to 50 mol, more preferably from 1 to 5 mol, per mol of 6-isopropenyl-3-methyl-9-decenol (4).

Examples of the catalyst used in the transesterification include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; bases such as sodium methoxide, sodium ethoxide, potassium t-butoxide, and 4-dimethylaminopyridine; salts such as sodium cyanide, potassium cyanide, sodium acetate, potassium acetate, calcium acetate, tin acetate, aluminum acetate, aluminum acetoacetate, and alumina; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide.

The catalyst may be used alone or in combination thereof, if necessary. The catalyst may be commercially available one.

An amount of the catalyst used in the transesterification is preferably from 0.001 mol to 1 mol, more preferably from 0.01 to 0.05 mol, per mol of 6-isopropenyl-3-methyl-9-decenol (4).

Examples of a solvent used in the transesterification include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; and ester solvents such as ethyl acetate and butyl acetate.

The solvent may be used alone or in combination thereof, if necessary. Depending on reaction conditions in the transesterification, the transesterification may be carried out without any solvent, but only with an alcohol compound by-produced in the transesterification, besides the acetate ester, and the catalyst. The solvent may be commercially available one.

An amount of the solvent used in the transesterification is preferably from 0 to 2000 g, more preferably from 0 to 500 g, per mol of 6-isopropenyl-3-methyl-9-decenol (4) in view of the economy.

A reaction temperature of the transesterification may be appropriately selected, depending on an acetate ester and a catalyst to be used. Typically, the reaction temperature is preferably from 0° C. to 200° C., more preferably from 50° C. to 160° C. When the transesterification is facilitated by removing the alcohol formed from the acetate ester, the reaction temperature is preferably a boiling point of the alcohol to be removed or above at normal pressure or at a reduced pressure.

A reaction time of the transesterification may be arbitrarily set and may be optimized by monitoring the reaction progress with gas chromatography (GC) or thin layer chromatography (TLC). The reaction time is typically and preferably from 5 minutes to 240 hours.

(iv) Conversion of 6-isopropenyl-3-methyl-9-decenol (4) into an alkylating Agent, Followed by acetoxylation with acetic Acid or the Like Typically, the conversion of 6-isopropenyl-3-methyl-9-decenol (4) into an alkylating agent, and subsequent acetoxylation with acetic acid or the like may be carried out by converting 6-isopropenyl-3-methyl-9-decenol (4) into its corresponding alkylating agent such as a halide, for instance, a chloride, a bromide, or an iodide, or a sulfonate ester such as a methanesulfonate ester, a benzenesulfonate ester, or a p-toluenesulfonate ester, and reacting the obtained alkylating agent with acetic acid in the presence of a base. The reaction may be also carried out without a base, and using an easily available metal acetate such as sodium acetate or potassium acetate instead of acetic acid.

The conversion of 6-isopropenyl-3-methyl-9-decenol (4) into its corresponding alkylating agent may be followed immediately by the acetoxylation in one step. Alternatively, after the conversion of 6-isopropenyl-3-methyl-9-decenol (4) into its corresponding alkylating agent, the organic phase is washed, the solvent is removed, and the alkylating agent is, if necessary, purified, and then the acetoxylation may be conducted.

The conversion of 6-isopropenyl-3-methyl-9-decenol (4) into its corresponding alkylating agent may be done in a manner in which 6-isopropenyl-3-methyl-9-decenol (4) is converted into a chloride, a bromide, or an iodide using a halogenating agent. 6-isopropenyl-3-methyl-9-decenol (4) is converted into a sulfonate ester using a sulfonylating agent.

Examples of the halogenating agent include chlorinating agents such as hydrochloric acid, phosphorous trichloride, thionyl chloride, carbon tetrachloride, methanesulfonyl chloride, and p-toluenesulfonyl chloride; brominating agents such as hydrobromic acid, phosphorus tribromide, thionyl bromide, and carbon tetrabromide; and iodinating agents such as hydroiodic acid, potassium iodide, and phosphorus triiodide.

Examples of the sulfonylating agent include methanesulfonyl chloride, benzenesulfonyl chloride, and p-toluenesulfonyl chloride.

An amount of the halogenating agent or sulfonylating agent used in the conversion of 6-isopropenyl-3-methyl-9-decenol (4) into an alkylating agent is preferably from 1 to 50 mol, more preferably from 1 to 10 mol, per mol of 6-isopropenyl-3-methyl-9-decenol (4) in view of the economy.

Examples of a solvent used in the conversion of 6-isopropenyl-3-methyl-9-decenol (4) into an alkylating agent include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; ester solvents such as ethyl acetate and butyl acetate; and aprotic polar solvents such as N,N-dimethylformamide, N,N-dimethylacetamide, dimethyl sulfoxide, and hexamethylphosphoric triamide.

The solvent may be used alone or in combination thereof, if necessary. The conversion may be carried out without a solvent. The solvent may be commercially available one.

An amount of the solvent used in the conversion of 6-isopropenyl-3-methyl-9-decenol (4) into an alkylating agent is preferably from 0 to 2000 g, more preferably from 0 to 500 g, per mol of 6-isopropenyl-3-methyl-9-decenol (4) in view of the economy.

A reaction temperature of the conversion of 6-isopropenyl-3-methyl-9-decenol (4) into an alkylating agent is preferably from −30 to 250° C., more preferably from 0 to 180° C., in view of the reactivity and yield.

An amount of the acetic acid or the metal acetate salt used in the acetoxylation reaction of the obtained alkylating agent is preferably from 1 mol to 50 mol, more preferably from 1 to 10 mol, per mol of the alkylating agent in view of the economy.

Examples of the base used in the acetoxylation reaction of the obtained alkylating agent include amines such as triethylamine, pyridine, N,N-dimethylaminopyridine, and dimethylaniline; organolithium compounds such as n-butyllithium, methyllithium, and phenyllithium; metal hydroxides such as sodium hydroxide and potassium hydroxide; metal carbonates such as potassium carbonate, sodium carbonate, and sodium bicarbonate; and metal hydrides such as sodium hydride and potassium hydride.

An amount of the base used in the acetoxylation reaction of the obtained alkylating agent is preferably from 1 to 50 mol, more preferably from 1 to 10 mol, per mol of the alkylating agent in view of the economy.

Examples of a solvent used in the acetoxylation reaction of the obtained alkylating agent include halogenated solvents such as methylene chloride and chloroform; hydrocarbon solvents such as hexane, heptane, benzene, and toluene; ether solvents such as diethyl ether, tetrahydrofuran, 1,4-dioxane, and ethylene glycol dimethyl ether; nitrile solvents such as acetonitrile; ketone solvents such as acetone, methyl ethyl ketone, and diisobutyl ketone; ester solvents such as ethyl acetate and butyl acetate; and aprotic polar solvents such as N,N-dimethylformamide, N,N-dimethylacetamide, dimethyl sulfoxide, and hexamethylphosphoric triamide.

The solvent may be used alone or in combination thereof, if necessary. Depending on an alkylating agent to be used, the acetoxylation reaction may be carried out without a solvent.

An amount of the solvent used in the acetoxylation reaction of the obtained alkylating agent is preferably from 0 g to 2000.0 g, more preferably from 0 g to 500.0 g, per mol of the alkylating agent in view of the economy.

A reaction temperature of the acetoxylation reaction of the obtained alkylating agent is preferably from −30 to 250° C., more preferably from 25 to 180° C., in view of the reactivity and yield.

A reaction time of the acetoxylation may be arbitrarily set and may be optimized by monitoring the reaction progress with gas chromatography (GC) or thin layer chromatography (TLC). The reaction time is typically and preferably from 5 minutes to 240 hours.

A crude product, 6-isopropenyl-3-methyl-9-decenyl acetate (5), obtained in the acetoxylation may be purified in any purification method used in ordinary organic synthesis, such as distillation or various chromatography. Distillation is particularly preferred in view of the industrial economy.

[4] Step A

Step A to obtain the 2-methyl-2,6-heptadiene compound (1) will be described below. The 2-methyl-2,6-heptadiene compound (1) is synthesized by converting the hydroxyl group of 2-methyl-2,6-heptadienol (6), as shown in the following chemical reaction formula.

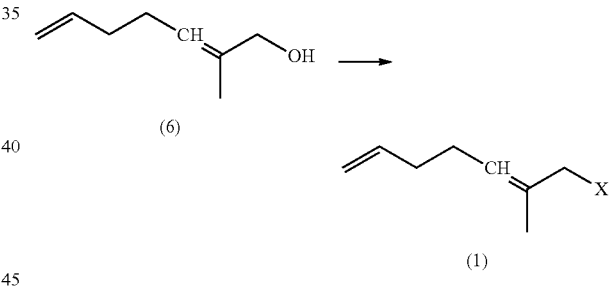

2-Methyl-2,6-heptadienol (6) may be (Z)-2-methyl-2,6-heptadienol of the following formula (6a) or (E)-2-methyl-2,6-heptadienol of the following formula (6b). 2-Methyl-2,6-heptadienol (6) may be either isomer or a combination of the isomers.

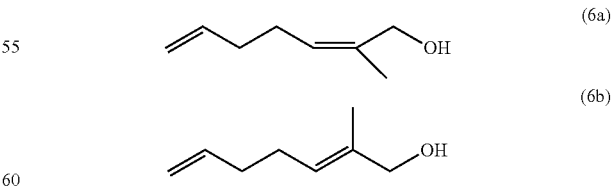

A process for preparing 2-methyl-2,6-heptadienol (6) is not particularly limited. For example, 2-methyl-2,6-heptadienol (6) may be obtained by a reduction of a 2-methyl-2,6-heptadienoate ester with a reducing agent.

When the leaving group X is an acyloxy group, the conversion of the hydroxyl group of 2-methyl-2,6-heptadienol (6) is an esterification reaction. The esterification reaction may be any known ester formation method, for example, (i) a reaction with an acylating agent, (ii) a reaction with a carboxylic acid, (iii) a transesterification, and (iv) conversion of the hydroxyl group of 2-methyl-2,6-heptadienol (6) into a leaving group, followed by a reaction with a carboxylic acid.

(i) Reaction with an acylating Agent

The reaction with an acylating agent may be carried out by reacting 2-methyl-2,6-heptadienol (6) with an acylating agent and a base in this order, in the reversed order or simultaneously in a single solvent or a mixed solvent.

Examples of the acylating agent include acyl halides such as acyl chloride and acyl bromide; carboxylic mixed anhydrides such as carboxylic anhydride, carboxylic/trifluoroacetic mixed anhydride, carboxylic/methanesulfonic mixed anhydride, carboxylic/trifluoromethanesulfonic mixed anhydride, carboxylic/benzenesulfonic mixed anhydride, and carboxylic/p-toluenesulfonic mixed anhydride; and p-nitrophenyl carboxylate.

Specific examples of the acyl chloride include acetyl chloride, propionyl chloride, crotonoyl chloride, and benzoyl chloride. Examples of the carboxylic anhydride include acetic anhydride and propionic anhydride.

An amount of the acylating agent used is preferably from 1 to 500 mol, more preferably from 1 to 50 mol, and even more preferably from 1 to 5 mol, per mol of 2-methyl-2,6-heptadienol (6).

Examples of a base used in the reaction with an acylating agent include N,N-diisopropylethylamine, N,N-dimethylaniline, N,N-diethylaniline, pyridine, 2-ethylpyridine, and 4-dimethylaminopyridine.

An amount of the base used is from 1 to 500 mol per mol of 2-methyl-2,6-heptadienol (6).

A solvent used in the reaction with an acylating agent may be the base itself described above. Examples of the solvent include chlorinated solvents such as methylene chloride, chloroform, and trichloroethylene; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, and 1,4-dioxane; nitriles such as acetonitrile; ketones such as acetone and 2-butanone; esters such as ethyl acetate and n-butyl acetate; and aprotic polar solvents such as N,N-dimethylformamide, dimethyl sulfoxide, and hexamethylphosphoric triamide.

The solvent may be used alone or in combination thereof, if necessary. The solvent may be commercially available one.

An amount of the solvent used is preferably from 10 to 1,000,000 g per mol of 2-methyl-2,6-heptadienol (6).

The reaction with the acylating agent such as a carboxylic anhydride, a carboxylic mixed anhydride, and p-nitrophenyl carboxylate may be carried out in the presence of an acid catalyst instead of the base.

Examples of the acid catalyst include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium (IV) oxide.

The acid catalyst may be used alone or in combination thereof, if necessary. The acid catalyst may be commercially available one.

An amount of the acid catalyst used in the reaction with an acylating agent such as carboxylic anhydride, carboxylic mixed anhydride, or p-nitrophenyl carboxylate is preferably from 0.0001 to 100 mol.

A reaction temperature of the reaction with an acylating agent may be appropriately selected, depending on an acylating agent and/or reaction conditions. Typically, the reaction temperature is preferably from −50° C. to a boiling point of the solvent, more preferably from −20° C. to room temperature (5° C. to 35° C., hereinafter the same).

A reaction time of the reaction with an acylating agent may be arbitrarily set and may be optimized by monitoring the reaction progress with gas chromatography (GC) or thin layer chromatography (TLC). The reaction time is typically and preferably from 5 minutes to 240 hours.

(ii) Reaction with a carboxylic Acid

The reaction with a carboxylic acid is a dehydration reaction between 2-methyl-2,6-heptadienol (6) and a carboxylic acid and is carried out typically in the presence of an acid catalyst.

Specific examples of the carboxylic acid used in the reaction between 2-methyl-2,6-heptadienol (6) and a carboxylic acid include linear saturated carboxylic acids such as formic acid, acetic acid, propionic acid, butyric acid, valeric acid, and caproic acid; branched saturated carboxylic acids such as isobutyric acid, isovaleric acid, 4-methylpentanoic acid, 2-methylbutanoic acid, and pivalic acid; linear unsaturated carboxylic acids such as acrylic acid, crotonic acid, and 3-butenoic acid; branched unsaturated carboxylic acids such as methacrylic acid, senecioic acid, tiglic acid, angelic acid, 3-methyl-4-pentenoic acid, and 4-methyl-4-pentenoic acid; and aromatic carboxylic acids such as benzoic acid.

An amount of the carboxylic acid used is preferably from 1 to 500 mol, more preferably from 1 to 50 mol, and even more preferably from 1 to 5 mol, per mol of 2-methyl-2,6-heptadienol (6).

In the reaction between 2-methyl-2,6-heptadienol (6) and a carboxylic acid, an acid catalyst may be used. The acid catalyst is those mentioned for the reaction with an acylating agent. An amount of the acid catalyst used is preferably from 0.0001 to 100 mol, more preferably from 0.001 to 1 mol, and even more preferably from 0.01 to 0.05 mol, per mol of 2-methyl-2,6-heptadienol (6).

A solvent and its amount used in the reaction between 2-methyl-2,6-heptadienol (6) and a carboxylic acid are same as those mentioned for the reaction with an acylating agent.

A reaction temperature of the reaction between 2-methyl-2,6-heptadienol (6) and a carboxylic acid may be appropriately selected, depending on reaction conditions. Typically, the reaction temperature is preferably from −50° C. to a boiling point of the solvent, more preferably from room temperature to a boiling point of the solvent.

The reaction may be done in a solvent including hydrocarbons such as hexane, heptane, benzene, toluene, xylene, and cumene, while removing the formed water from the reaction system by azeotropic distillation. Alternatively, water may be distilled off with refluxing at a boiling point of the solvent at normal pressure, or distilled off at a lower temperature than a boiling point of the solvent at a reduced pressure.

A reaction time of the reaction with a carboxylic acid may be arbitrarily set and may be optimized by monitoring the reaction progress with gas chromatography (GC) or thin layer chromatography (TLC). The reaction time is typically and preferably from 5 minutes to 240 hours.

(iii) Transesterification

The transesterification is carried out by reacting 2-methyl-2,6-heptadienol (6) with an alkyl carboxylate in the presence of a catalyst and removing a formed alcohol. The alkyl carboxylate is preferably a primary alkyl ester of a carboxylic acid.

Methyl carboxylate, ethyl carboxylate, and n-propyl carboxylate are preferred in view of the price and/or easiness of reaction.

Examples of the carboxylic acid may be those for the esterification reaction with a carboxylic acid.

An amount of the alkyl carboxylate used is preferably from 1 to 500 mol, more preferably from 1 to 50 mol, and even more preferably from 1 to 5 mol, per mol of 2-methyl-2,6-heptadienol (6).

Examples of the catalyst used in the transesterification include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; bases such as sodium methoxide, sodium ethoxide, potassium t-butoxide, and 4-dimethylaminopyridine; salts such as sodium cyanide, potassium cyanide, sodium acetate, potassium acetate, calcium acetate, tin acetate, aluminum acetate, aluminum acetoacetate, and alumina; Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide.

The catalyst may be used alone or in combination thereof, if necessary. The catalyst may be commercially available one.

An amount of the catalyst used is preferably from 0.0001 to 100 mol, more preferably from 0.001 to 1 mol, and even more preferably from 0.01 to 0.05 mol, per mol of 2-methyl-2,6-heptadienol (6).

The transesterification may be carried out in the alkyl carboxylate as a solvent without any additional solvent, or with an auxiliary solvent. It is preferred not to use any additional solvent, because this does not require extra operations such as concentration or solvent recovery.

Examples of the solvent used in the transesterification include hydrocarbons such as hexane, heptane, benzene, toluene, xylene, and cumene; and ethers such as diethyl ether, dibutyl ether, diethylene glycol diethyl ether, diethylene glycol dimethyl ether, tetrahydrofuran, and 1,4-dioxane.

The solvent may be used alone or in combination thereof, if necessary. The solvent may be commercially available one.

An amount of the solvent used is preferably from 10 to 1,000,000 g, per mol of 2-methyl-2,6-heptadienol (6).

A reaction temperature of the transesterification may be appropriately selected, depending on an alkyl carboxylate and/or reaction conditions. The transesterification is typically carried out under heating. In view of the easiness of reaction, the transesterification is preferably carried out around a boiling point of a lower $C_{1-3}$ alcohol that generates in the transesterification, that is, methanol, ethanol, or 1-propanol, while distilling off the formed low-boiling lower alcohol. The alcohol may be distilled off at a lower temperature than its boiling point at a reduced pressure.

A reaction time of the transesterification may be arbitrarily set and may be optimized by monitoring the reaction progress with gas chromatography (GC) or thin layer chromatography (TLC). The reaction time is typically and preferably from 5 minutes to 240 hours.

(iv) Conversion of the hydroxyl Group of 2-methyl-2,6-heptadienol (6) into a Leaving Group, Followed by a Reaction with a carboxylic Acid The conversion of the hydroxyl group of 2-methyl-2,6-heptadienol (6) into a leaving group and the subsequent reaction with a carboxylic acid may be carried out by, for example, converting the hydroxyl group of 2-methyl-2,6-heptadienol (6) to a leaving group such as a halogen atom such as a chlorine atom, a bromine atom, or an iodine atom; an alkanesulfonyloxy group such as a methanesulfonyloxy group or a trifluoromethanesulfonyloxy group; or an arenesulfonyloxy group such as a benzenesulfonyloxy group or a p-toluenesulfonyloxy group, and reacting the formed compound with a carboxylic acid in a solvent in the presence of a base. The conversion may be also carried out without a base, and using an easily-available metal carboxylate salt such as sodium carboxylate or potassium carboxylate, instead of the carboxylic acid.

Examples of the carboxylic acid may be those for the reaction with a carboxylic acid.

An amount of the carboxylic acid used is preferably from 1 to 500 mol, more preferably from 1 to 50 mol, and even more preferably from 1 to 5 mol, per mol of 2-methyl-2,6-heptadienol (6).

Examples of the base include amines such as triethylamine, pyridine, N,N-dimethylaminopyridine, and dimethylaniline; organolithium compounds such as n-butyllithium, methyllithium, and phenyllithium; metal hydroxides such as sodium hydroxide and potassium hydroxide; metal carbonates such as potassium carbonate, sodium carbonate, and sodium bicarbonate; and metal hydrides such as sodium hydride and potassium hydride.

An amount of the base used is preferably from 1 to 50 mol, more preferably from 1 to 10 mol, per mol of the alkylating agent in view of the economy.

A solvent, an amount of the solvent, a reaction time, and a reaction temperature in the conversion of the hydroxyl group of 2-methyl-2,6-heptadienol (6) into a leaving group and the reaction with a carboxylic acid are same as those mentioned for the reaction between 2-methyl-2,6-heptadienol (6) and the acylating agent.

A carboxylate salt such as sodium carboxylate, lithium carboxylate, potassium carboxylate, or ammonium carboxylate may be used instead of the carboxylic acid in a combination with the base. An amount of the carboxylate salt is same as the amount of the carboxylic acid in the esterification with a carboxylic acid.

When the leaving group X is an alkanesulfonyloxy group, the hydroxyl group of 2-methyl-2,6-heptadienol (6) is converted using an alkanesulfonylating agent. The reaction with the alkanesulfonylating agent may be carried out by reacting 2-methyl-2,6-heptadienol (6) with the alkanesulfonylating agent and a base in this order, in the reversed order or simultaneously in a single solvent or a mixed solvent.

Examples of the alkanesulfonylating agent include alkanesulfonic anhydrides that may be substituted, such as methanesulfonic anhydride, ethanesulfonic anhydride, and trifluoromethanesulfonic anhydride; and alkanesulfonyl halides that may be substituted, such as methanesulfonyl chloride, ethanesulfonyl chloride, and trifluoromethanesulfonyl chloride.

An amount of the alkanesulfonylating agent used is preferably from 1 to 500 mol, more preferably from 1 to 50 mol, and even more preferably from 1 to 5 mol, per mol of 2-methyl-2,6-heptadienol (6).

Examples of the base used in the reaction with the alkanesulfonylating agent include organic bases including amines such as diethylamine, triethylamine, diisopropylethylamine, tri-n-propylamine, tri-n-butylamine, diazabicyclononene (DBN), diazabicycloundecene (DBU), N-methylmorpholine, and N,N-dimethylaniline; pyridines such as pyridine, methylethylpyridine, lutidine, and N,N-dimethyl-4-aminopyridine; imidazoles; and pyrazoles; and inorganic bases including alkaline metal or alkaline-earth metal hydroxides such as lithium hydroxide, sodium hydroxide, potassium hydroxide, magnesium hydroxide, calcium hydroxide, and barium hydroxide; alkaline metal or alkaline-earth metal carbonates such as sodium carbonate, potassium carbonate, cesium carbonate, magnesium carbonate, calcium carbonate, and barium carbonate; metal alkoxides such as sodium ethoxide; alkaline metal amides such as sodium amide and lithium amide; and alkaline metal hydrides such as sodium hydride and lithium hydride. Preferred examples include pyridine and triethylamine.

An amount of the base used is preferably from 1 to 500 mol, per mol of 2-methyl-2,6-heptadienol (6).

The solvent used in the reaction with an alkanesulfonylating agent may be the base itself described above. Examples of the solvent include chlorinated solvents such as methylene chloride, chloroform, and trichloroethylene; hydrocarbons such as hexane, heptane, benzene, toluene, xylene, and cumene; ethers such as diethyl ether, dibutyl ether, diethyleneglycol diethyl ether, diethyleneglycol dimethyl ether, tetrahydrofuran, and 1,4-dioxane; nitriles such as acetonitrile; ketones such as acetone and 2-butanone; esters such as ethyl acetate and n-butyl acetate; and aprotic polar solvents such as N,N-dimethylformamide, dimethyl sulfoxide, and hexamethylphosphoric triamide.

The solvent may be used alone or in combination thereof, if necessary. The solvent may be commercially available one.

An amount of the solvent used is preferably from 10 to 1,000,000 g, per mol of 2-methyl-2,6-heptadienol (6).

A reaction temperature of the reaction with an alkanesulfonylating agent may be appropriately selected, depending on an alkanesulfonylating agent and/or reaction condition to be used. Typically, the reaction temperature is preferably from −50° C. to a boiling point of the solvent, more preferably from −20° C. to room temperature (5° C. to 35° C.).

A reaction time of the reaction with an alkanesulfonylating agent may be arbitrarily set and may be optimized by monitoring the reaction progress with gas chromatography (GC) or thin layer chromatography (TLC). The reaction time is typically and preferably from 5 minutes to 240 hours.

When the leaving group X is an arenesulfonyloxy group, the conversion of the hydroxyl group of 2-methyl-2,6-heptadienol (6) is carried out using an arenesulfonylating agent. This reaction with an arenesulfonylating agent may be carried out by reacting 2-methyl-2,6-heptadienol (6) with the arenesulfonylating agent and a base in this order, in the reversed order or simultaneously, in a single solvent or a mixed solvent.

Examples of the arenesulfonylating agent include arenesulfonic anhydrides such as benzenesulfonic anhydride and p-toluenesulfonic anhydride; and arenesulfonyl halides such as benzenesulfonyl chloride and p-toluenesulfonyl chloride.

An amount of the arenesulfonylating agent used is preferably from 1 to 500 mol, more preferably from 1 to 50 mol, and even more preferably from 1 to 5 mol, per mol of 2-methyl-2,6-heptadienol (6).

The base, an amount of the base, a solvent, an amount of the solvent, a reaction time, and a reaction temperature in the reaction with the arenesulfonylating agent are same as those for the reaction between 2-methyl-2,6-heptadienol (6) and the alkanesulfonylating agent.

When the leaving group X is a halogen atom, the conversion of the hydroxyl group of 2-methyl-2,6-heptadienol (6) is carried out using a halogenating agent. This reaction with the halogenating agent is carried out by reacting 2-methyl-2,6-heptadienol (6) with the halogenating agent and a base in order, in the reversed order or simultaneously in a single solvent or a mixed solvent.

Examples of the halogenating agent include thionyl halides such as thionyl chloride and thionyl bromide; phosphorus halide compounds such as phosphorous trichloride, phosphorus tribromide, phosphorous pentachloride, and phosphorus pentabromide; phosphorus oxyhalide compounds such as phosphorus oxychloride and phosphorus oxybromide; and aromatic phosphorus halide compounds such as dichlorotriphenylphosphorane and dibromotriphenylphosphorane.

When sulfonyl halides such as methanesulfonyl chloride, ethanesulfonyl chloride, or trifluoromethanesulfonyl chloride is used instead of the halogenating agent, the hydroxyl group of 2-methyl-2,6-heptadienol (6) is sulfonylated, which is then substituted with a halogen atom corresponding to the sulfonic halide by, if necessary, heating.

When the hydroxyl group is sulfonylated with a sulfonylating agent other than sulfonyl halides, or is halogenated with a halogenating agent, the formed compound may be converted into the corresponding halide using a halogenating agent such as a metal halide or a quaternary onium salt.

Examples of the metal halide include lithium bromide, sodium bromide, potassium bromide, lithium iodide, sodium iodide, and potassium iodide.

Examples of the quaternary onium salt include tetraethylammonium bromide, tetrabutylammonium bromide, tetrabutylphosphonium bromide, tetraethylammonium iodide, tetrabutylammonium iodide, and tetrabutylphosphonium iodide.

An amount of the halogenating agent used is preferably from 1 to 500 mol, more preferably from 1 to 50 mol, and even more preferably from 1 to 5 mol, per mol of 2-methyl-2,6-heptadienol (6).

A base, an amount of the base, a solvent, an amount of the solvent, a reaction time, and a reaction temperature in the reaction with the halogenating agent are same as those mentioned for the reaction between 2-methyl-2,6-heptadienol (6) and the alkanesulfonylating agent.

When the 2-methyl-2,6-heptadiene compound (1) having a leaving group X at position 1, obtained in the conversion of the hydroxyl group, has a sufficient purity, the 2-methyl-2,6-heptadiene compound (1) may be used as such in a subsequent step. Alternatively, the crude product may be purified in any purification method used in usual organic synthesis, such as distillation or various chromatography. Distillation is particularly preferred in view of the industrial economy.

In an embodiment of the present invention comprising steps A to D, the 6-isopropenyl-3-methyl-9-decene compound (3) having a protected hydroxyl group at position 1 is deprotected to form 6-isopropenyl-3-methyl-9-decenol (4) in step C and, then, 6-isopropenyl-3-methyl-9-decenol (4) is acetylated to form a target compound, 6-isopropenyl-3-methyl-9-decenyl acetate (5) in step D. The present inventors have further found that 6-isopropenyl-3-methyl-9-decenyl acetate (5) may be obtained using the acetylating agent in deprotection conditions instead of steps C and D, as shown in the following chemical reaction formula In other words, it is thought that in a case where the acetylating agent is used in deprotection conditions, an acetylation reaction occurs after the deprotection reaction, so that 6-isopropenyl-3-methyl-9-decenyl acetate (5) is obtained in a single step. Whether an acetylation reaction occurs or not after the deprotection reaction depends on, for example, a protecting group in the 6-isopropenyl-3-methyl-9-decene compound (3) having the protected hydroxyl group at position 1. Examples of such a protecting group include those that can be deprotected with an acid, specifically oxyalkyl groups such as a 1-ethoxyethyl group. For example, an acetylating agent such as acetic anhydride may promote the acetylation after the deprotection reaction in a single step in the presence of an acid catalyst. Examples of the acid catalyst include inorganic acids such as hydrochloric acid, hydrobromic acid, nitric acid, and sulfuric acid; organic acids such as trichloroacetic acid, trifluoroacetic acid, methanesulfonic acid, benzenesulfonic acid, and p-toluenesulfonic acid; Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide; and metal acetate salts such as sodium acetate and potassium acetate. Preferably, in a case where the acetylating agent is acetic anhydride and the acid catalyst is p-toluenesulfonic acid, an acetylation reaction occurs after the deprotection reaction, so that the deprotection reaction and the acetylation reaction occurs in a single step (see Example 19 below).

Thus, there are provided a process for efficiently and industrially preparing 6-isopropenyl-3-methyl-9-decenyl acetate (5), and a 2-methyl-2,6-heptadiene compound (1') and a 2-methyl-2,6-heptadiene compound (1"), both of which are useful intermediate materials for the aforesaid process.

EXAMPLES

The present invention will be further described with reference to the following Examples. It should be understood that the present invention is not limited to or by the following Examples.

The term "purity" as used herein means an area percentage obtained by gas chromatography (GC), unless otherwise specified. The term "production ratio" is a ratio of area percentages obtained by GC. The term "yield" is calculated from the area percentages obtained by GC.

A sample for measuring the spectrum was obtained by purifying a crude product in some cases.

In the Examples, monitoring of the reactions and calculation of the yields were carried out in the following GC conditions.
GC conditions: GC: Capillary gas chromatograph GC-2014 (Shimadzu Corporation); column: DB-5, 0.25 mm×0.25 mmϕ×30 m; carrier gas: He (1.55 mL/min), detector: FID; column temperature: 100° C., elevated in a rate of 10° C./min, and up to 230° C.

In the Examples, monitoring of some of the reactions was carried out by thin layer chromatography (TLC). In the data from TLC, the solvent indicated within parentheses represents an elution solvent or developing solvent used, and the ratio is expressed as a volume ratio.

The yield was calculated according to the following equation in consideration of purities (% GC) of a starting material and a product.

Yield (%)={[(weight of a product obtained by a reaction×% GC)/molecular weight of a product]·[(weight of a starting material in a reaction×% GC)/molecular weight of a starting material]}×100

The term "crude yield" refers to a yield of a crude product obtained without purification.

Example 1

Preparation of 2-methyl-2,6-heptadienyl acetate (1':X'=OAc)

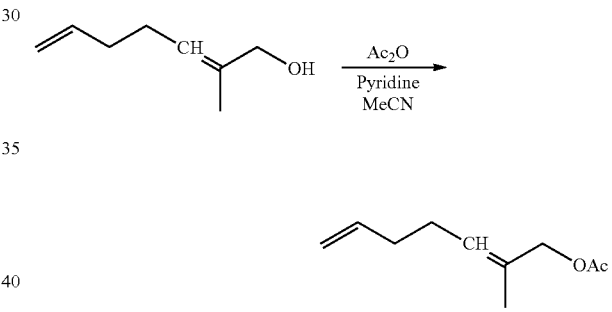

In a reactor were placed 2-methyl-2,6-heptadienol (6) (3.00 g: 0.021 mol), pyridine (5.81 g: 0.73 mol), acetic anhydride (Ac$_2$O) (3.59 g: 0.029 mol), and acetonitrile (MeCN) (10 ml) in a nitrogen atmosphere and stirred at room temperature for 14 hours and 40 minutes. Pure water (20 g) and hexane (20 g) were then added and stirred for 30 minutes, and the organic phase was separated. The separated organic phase was subjected to post-treatment, i.e., usual washing, drying, and concentration, to obtain a crude product, 2-methyl-2,6-heptadienyl acetate (1':X'=OAc) (3.60 g) in a crude yield of 90.45%.

The following are spectrum data of 2-methyl-2,6-heptadienyl acetate (1': X'=OAc) thus obtained.

IR (D-ATR): ν=3078, 2975, 2922, 1741, 1641, 1440, 1367, 1233, 1023, 984, 957, 913, 634, 607, 560 cm$^{-1}$.

$^1$H-NMR (500 MHz, CDCl$_3$): δ=1.74 (3H, s-like), 2.06 (3H, s), 2.07-2.19 (4H, m), 4.57 (2H, s), 4.94-5.03 (2H, m), 5.39 (1H, t, J=7.6 Hz), 5.75-5.83 (1H, m) ppm.

$^{13}$C-NMR (125 MHz, CDCl$_3$): δ=20.90, 21.37, 27.09, 33.75, 63.12, 113.89, 129.98, 130.15, 137.93, 171.08 ppm.

GC-MS (EI, 70 eV): 27, 43, 55, 67, 79, 93, 108, 126, 140, 153, 168.

Example 2

Preparation of 2-methyl-2,6-heptadienyl isobutyrate
(1':X'=OC(=O)CH(CH$_3$)$_2$)

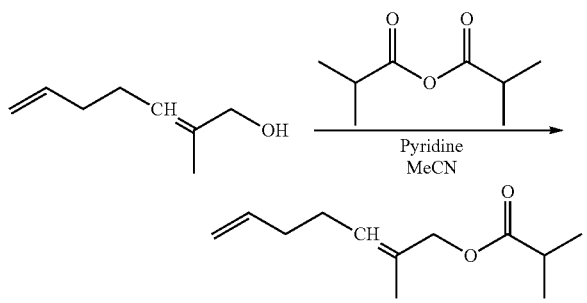

In a reactor were placed 2-methyl-2,6-heptadienol (6) (3.00 g: 0.017 mol), pyridine (6.64 g: 0.84 mol), isobutyric anhydride (5.32 g: 0.034 mol), and acetonitrile (MeCN) (10 ml) in a nitrogen atmosphere and stirred at room temperature for 7 hours. Pure water (20 g) and hexane (20 g) were then added and stirred for 30 minutes, and the organic phase was separated. The separated organic phase was subjected to post-treatment, i.e., washing, drying, and concentration, to obtain a crude product, 2-methyl-2,6-heptadienyl isobutyrate (1': X'=OC(=O)CH(CH$_3$)$_2$) (4.62 g) in a crude yield of 100%.

The following are spectrum data of 2-methyl-2,6-heptadienyl isobutyrate (1':X'=OC(=O)CH(CH$_3$)$_2$) thus obtained.

IR (D-ATR): ν=3078, 2975, 2938, 2879, 1814, 1736, 1641, 1471, 1388, 1354, 1252, 1190, 1154, 1117, 1068, 1021, 965, 913, 756, 642 cm$^{-1}$.

$^1$H-NMR (500 MHz, CDCl$_3$): δ=1.16 (6H, d, J=7.3 Hz), 1.73 (3H, s-like), 2.06-2.20 (4H, m), 2.51-2.59 (1H, m), 4.57 (2H, s), 4.94-5.03 (2H, m), 5.39 (1H, t, J=7.5 Hz), 5.75-5.83 (1H, m) ppm.

$^{13}$C-NMR (125 MHz, CDCl$_3$): δ=18.24, 18.97, 21.30, 27.09, 33.79, 34.02, 62.96, 114.86, 129.66, 130.41, 137.98, 177.10 ppm.

GC-MS (EI, 70 eV): 27, 43, 55, 71, 81, 93, 108, 126, 142, 155, 168, 181, 196.

Example 3

Preparation of 2-methyl-2,6-heptadienyl bromide
(1: X=Br)

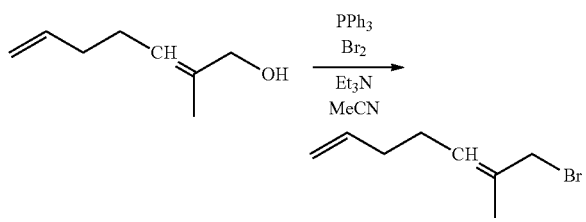

In a reactor were placed triphenylphosphine (PPh$_3$) (7.73 g: 0.029 mol) and acetonitrile (MeCN) (16.8 g) in a nitrogen atmosphere, and the mixture was cooled to an internal temperature of −5 to 5° C. Then, bromine (Br$_2$) (4.50 g: 0.028 mol) was added dropwise into the reactor over 15 minutes at an internal temperature of −5 to 5° C., and stirred at an internal temperature of −5 to 10° C. for 3 hours. Then, a liquid mixture of 2-methyl-2,6-heptadienol (6) (3.00 g: 0.021 mol) and triethylamine (Et$_3$N) (2.97 g: 0.029 mol) was added dropwise into the reactor over 30 minutes with the internal temperature being kept at −5 to 10° C., and stirred at an internal temperature of −5 to 10° C. for 1 hour. The mixture was then stirred at room temperature for 14 hours. Pure water (20 g) and hexane (20 g) was added into the reactor and stirred for 30 minutes, and the organic phase was separated. The separated organic phase was subjected to post-treatment, i.e., washing, drying, and concentration, to obtain a crude product, 2-methyl-2,6-heptadienyl bromide (1: X=Br) (3.33 g) in a crude yield of 71.43%.

The following are spectrum data of 2-methyl-2,6-heptadienyl bromide (1: X=Br) thus obtained.

IR (D-ATR): ν=3078, 3028, 2975, 2919, 2856, 2735, 1830, 1739, 1641, 1438, 1379, 1205, 1119, 1065, 992, 913, 847, 811, 769, 721, 696, 636, 542 cm$^{-1}$.

$^1$H-NMR (500 MHz, CDCl$_3$): δ=1.84 (3H, s-like), 2.07-2.19 (4H, m), 3.98 (2H, s), 4.97-5.03 (2H, m), 5.39 (1H, t-like, J=6.8 Hz), 5.75-5.85 (1H, m) ppm.

$^{13}$C-NMR (125 MHz, CDCl$_3$): δ=21.84, 27.39, 32.24, 33.24, 115.06, 130.79, 131.92, 137.83 ppm.

GC-MS (EI, 70 eV): 27, 41, 55, 67, 79, 93, 109, 119, 133, 147, 162, 175, 188.

Example 4

Preparation of 2-methyl-2,6-heptadienyl chloride
(1: X=Cl)

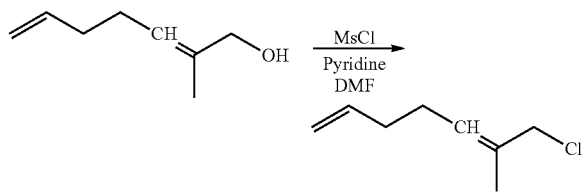

In a reactor were placed 2-methyl-2,6-heptadienol (6) (8.00 g: 0.056 mol), pyridine (7.97 g: 0.101 mol), and dimethylformamide (DMF) (10 ml) in a nitrogen atmosphere, and the mixture was cooled to an internal temperature of −5 to 5° C. and stirred for 15 minutes. Then, methanesulfonyl chloride (MSCl) (8.98 g: 0.078 mol) was added dropwise into the reactor over 10 minutes with the internal temperature being kept at −5 to 5° C. After the completion of the dropwise addition, the mixture was stirred at an internal temperature of −5 to 5° C. for 1 hour and further stirred at room temperature for 12 hours. Pure water (20 g) and hexane (20 g) were then added into the reactor and stirred for 30 minutes, and the organic phase was separated. The separated organic phase was subjected to post-treatment, i.e., washing, drying, and concentration, to obtain a crude product, 2-methyl-2,6-heptadienyl chloride (1: X=Cl) (4.36 g) in a crude yield of 48.21%.

The following are spectrum data of 2-methyl-2,6-heptadienyl chloride (1: X=Cl) thus obtained.

IR (D-ATR): ν=3078, 2975, 2934, 2921, 2854, 2735, 1831, 1728, 1641, 1443, 1380, 1257, 1119, 1077, 992, 913, 850, 815, 700, 641 cm$^{-1}$.

$^1$H-NMR (500 MHz, CDCl$_3$): δ=1.83 (3H, s-like), 2.07-2.21 (4H, m), 4.06 (2H, s), 4.97-5.03 (2H, m), 5.39 (1H, t-like, J=7.2 Hz), 5.75-5.85 (1H, m) ppm.

$^{13}$C-NMR (125 MHz, CDCl$_3$): δ=21.84, 27.25, 32.24, 33.55, 115.04, 130.39, 131.71, 137.84 ppm.

GC-MS (EI, 70 eV): 27, 41, 53, 67, 75, 87, 95, 103, 116, 129, 144.

Example 5

Preparation of 3-methyl-5-(tetrahydropyran-2-yloxy)pentylmagnesium chloride (2: M=MgZ$^1$, Z$^1$=Cl, R=2-tetrahydropyranyl group (THP)) and tetrahydro-2-(6-isopropenyl-3-methyl-9-decenyloxy)-2H-pyran (3: R=THP)

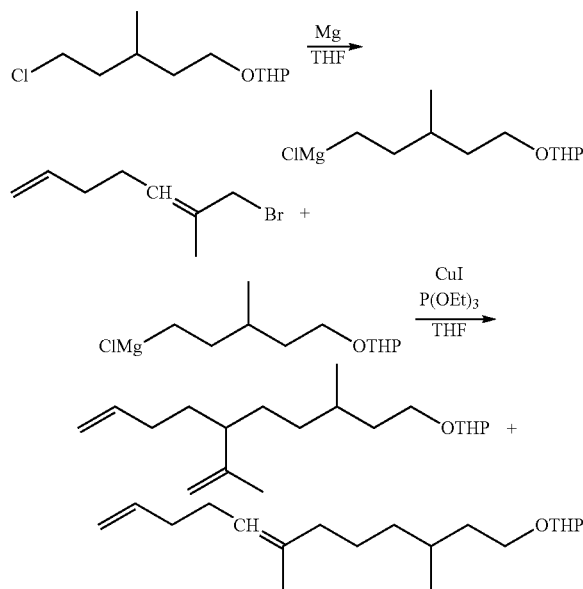

In a reactor were placed magnesium (0.19 g: 0.0078 mol) and tetrahydrofuran (THF) (0.7 g) in a nitrogen atmosphere, heated to 60° C., and stirred for 15 minutes. Then, a mixed solution of tetrahydro-2-(5-chloro-3-methylpentyloxy)-2H-pyran (1.7 g: 0.007 mol) and tetrahydrofuran (THF) (1.5 g) was added dropwise into the reactor over 30 minutes. After the completion of the dropwise addition, the mixture was stirred at an internal temperature of 50 to 60° C. for 3 hours to obtain 3-methyl-5-(tetrahydropyran-2-yloxy)pentylmagnesium chloride (2: M=MgZ$^1$, Z$^1$=Cl, R=THP). Then, 3-methyl-5-(tetrahydropyran-2-yloxy)pentylmagnesium chloride (2: M=MgZ$^1$, Z$^1$=Cl, R=THP) thus obtained was cooled to room temperature.

In another reactor were placed copper(I) iodide (CuI) (0.002 g), triethyl phosphite (P(OEt)$_3$) (0.003 g), tetrahydrofuran (THF) (4 ml), and 2-methyl-2,6-heptadienyl bromide (1: X=Br) (0.80 g: 0.004 mol) obtained according to Example 3 in a nitrogen atmosphere. The mixture was stirred and cooled to −78° C. to −50° C. The whole amount of 3-methyl-5-(tetrahydropyran-2-yloxy)pentylmagnesium chloride (2: M=MgZ$^1$, Z$^1$=Cl, R=THP) prepared above was added dropwise into the another reactor at −50° C. or below over 30 minutes. After the completion of the dropwise addition, the mixture was stirred for 3 hours. Pure water (10 g) and an aqueous solution of ammonium chloride (1 g) were added into the another reactor and stirred for 30 minutes, and then the organic phase was separated. The separated organic phase was subjected to post-treatment, i.e., washing, drying, and concentration, to obtain a crude product, tetrahydro-2-(6-isopropenyl-3-methyl-9-decenyloxy)-2H-pyran (3: R=THP) (1.24 g:

0.04 mol) in a crude yield of 10.00%. A production ratio of tetrahydro-2-(6-isopropenyl-3-methyl-9-decenyloxy)-2H-pyran (3: R=THP):tetrahydro-2-(3,7-dimethyl-7,11-dodecadienyloxy)-2H-pyran was 72:28.

The following are spectrum data of the crude product, tetrahydro-2-(6-isopropenyl-3-methyl-9-decenyloxy)-2H-pyran (3: R=THP) thus obtained.

IR (D-ATR): ν=3072, 2928, 2870, 1642, 1453, 1441, 1376, 1353, 1323, 1260, 1201, 1184, 1136, 1122, 1078, 1035, 991, 970, 908, 888, 870, 815 cm$^{-1}$.

$^1$H-NMR (500 MHz, CDCl$_3$): δ=0.86-0.89 (3H, m), 1.00-1.08 (1H, m), 1.16-2.10 (20H, m), 3.34-3.43 (1H, m), 3.47-3.53 (1H, m), 3.72-3.80 (1H, m), 3.83-3.89 (1H, m), 4.55-4.57 (1H, m), 4.63-4.65 (1H, m), 4.72-4.73 (1H, m), 4.90-5.02 (2H, m), 5.75-5.83 (1H, m) ppm.

$^{13}$C-NMR (125 MHz, CDCl$_3$): δ=17.68, 17.70, 17.79, 19.49, 19.62, 19.64, 19.73, 19.80, 19.92, 25.42, 25.48, 29.83, 30.03, 30.11, 30.53, 30.56, 30.63, 30.66, 30.77, 31.66, 32.56, 32.71, 34.70, 34.75, 34.78, 34.88, 36.38, 36.47, 36.82, 36.86, 46.95, 47.00, 47.07, 47.10, 62.28, 65.82, 65.86, 65.98, 94.61, 98.73, 98.91, 111.64, 111.73, 114.13, 139.08, 147.20, 147.32 ppm.

GC-MS (EI, 70 eV): 27, 41, 55, 69, 85, 109, 123, 149, 163, 182, 196, 210, 224, 240, 261, 276, 294.

Example 6

Preparation of 3-methyl-5-(tetrahydropyran-2-yloxy)pentylmagnesium chloride (2: M=MgZ$^1$, Z$^1$=Cl, R=THP) and tetrahydro-2-(6-isopropenyl-3-methyl-9-decenyloxy)-2H-pyran (3: R=THP)

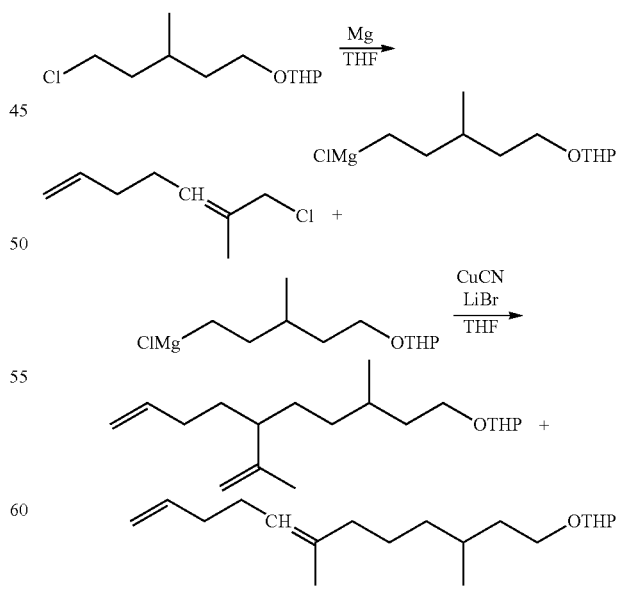

In a reactor were placed magnesium (0.26 g: 0.011 mol) and tetrahydrofuran (THF) (1 g) in a nitrogen atmosphere, heated to 60° C., and stirred for 10 minutes. Then, a mixed solution of tetrahydro-2-(5-chloro-3-methylpentyloxy)-2H-pyran (2.21 g: 0.01 mol) and tetrahydrofuran (THF) (2 g) was added dropwise into the reactor over 10 minutes. After the completion of the dropwise addition, the mixture was stirred at an internal temperature of 50 to 60° C. for 3 hours to obtain 3-methyl-5-(tetrahydropyran-2-yloxy)pentylmagnesium chloride (2: M=MgZ$^1$, Z$^1$=Cl, R=THP). Then, 3-methyl-5-(tetrahydropyran-2-yloxy)pentylmagnesium chloride (2: M=MgZ$^1$, Z$^1$=Cl, R=THP) thus obtained was cooled to −5 to 0° C.

A mixed solution of copper(I) cyanide (CuCN) (0.90 g), lithium bromide (LiBr) (1.74 g), and tetrahydrofuran (THF) (10 ml) was added dropwise into the reactor over 10 minutes, and then cooled to an internal temperature of −78 to −50° C. Then, a mixed solution of 2-methyl-2,6-heptadienyl chloride (1: X=Cl) (0.50 g: 0.002 mol) obtained according to Example 4 and THF (10 ml) was added dropwise into the reactor over 20 minutes. After the completion of the dropwise addition, the mixture was stirred at −78° C. to −50° C. for 1 hour. A mixture of pure water (20 g) and ammonium chloride (2 g) was added into the reactor and stirred for 30 minutes, and then the organic phase was separated. The separated organic phase was subjected to post-treatment, i.e., washing, drying, and concentration, to obtain a crude product, tetrahydro-2-(6-isopropenyl-3-methyl-9-decenyloxy)-2H-pyran (3: R=THP) (1.86 g: 0.003 mol) in a crude yield of 100%. A production ratio of tetrahydro-2-(6-isopropenyl-3-methyl-9-decenyloxy)-2H-pyran (3: R=THP):tetrahydro-2-(3,7-dimethyl-7,11-dodecadienyloxy)-2H-pyran was 99:1.

The spectrum data of tetrahydro-2-(6-isopropenyl-3-methyl-9-decenyloxy)-2H-pyran (3: R=THP) thus obtained were same as those obtained in Example 5.

Example 7

Preparation of 3-methyl-5-(tetrahydropyran-2-yloxy)pentylmagnesium chloride (2: M=MgZ$^1$, Z$^1$=Cl, R=THP) and tetrahydro-2-(6-isopropenyl-3-methyl-9-decenyloxy)-2H-pyran (3: R=THP)

In a reactor were placed magnesium (0.26 g: 0.01 mol) and tetrahydrofuran (THF) (1 g) in a nitrogen atmosphere, heated to 60° C., and stirred for 15 minutes. A mixed solution of tetrahydro-2-(5-chloro-3-methylpentyloxy)-2H-pyran (2.21 g: 0.01 mol) and tetrahydrofuran (THF) (2 g) was then added dropwise into the reactor over 30 minutes. After the completion of the dropwise addition, the mixture was stirred at an internal temperature of 50 to 60° C. for 3 hours to obtain 3-methyl-5-(tetrahydropyran-2-yloxy)pentylmagnesium chloride (2: M=MgZ$^1$, Z$^1$=Cl, R=THP). Then, 3-methyl-5-(tetrahydropyran-2-yloxy)pentylmagnesium chloride (2: M=MgZ$^1$, Z$^1$=Cl, R=THP) thus obtained was cooled to room temperature.

In another reactor were placed copper(I) bromide (CuBr) (1.29 g), lithium bromide (LiBr) (1.56 g), tetrahydrofuran (THF) (10 ml), and 2-methyl-2,6-heptadienyl chloride (1: X=Cl) (0.50 g: 0.003 mol) obtained according to Example 4, in a nitrogen atmosphere. The mixture was stirred and cooled to −78° C. to −50° C. The whole amount of 3-methyl-5-(tetrahydropyran-2-yloxy)pentylmagnesium chloride (2: M=MgZ$^1$, Z$^1$=Cl, R=THP) prepared above was then added dropwise into the another reactor at −50° C. or below over 50 minutes. After the completion of the dropwise addition, the mixture was stirred for 3 hours. A mixture of pure water (20 g) and ammonium chloride (2 g) was added into the another reactor and further stirred for 30 minutes, and then the organic phase was separated. The separated organic phase was subjected to post-treatment, i.e., washing, drying, and concentration, to obtain a crude product, tetrahydro-2-(6-isopropenyl-3-methyl-9-decenyloxy)-2H-pyran (3: R=THP) (2.13 g: 0.004 mol) in a crude yield of 100%. A production ratio of tetrahydro-2-(6-isopropenyl-3-methyl-9-decenyloxy)-2H-pyran (3: R=THP):tetrahydro-2-(3,7-dimethyl-7,11-dodecadienyloxy)-2H-pyran was 99:1.

The spectrum data of tetrahydro-2-(6-isopropenyl-3-methyl-9-decenyloxy)-2H-pyran (3: R=THP) thus obtained were same as those obtained in Example 5.

Example 8

Preparation of 3-methyl-5-(tetrahydropyran-2-yloxy)pentylmagnesium chloride (2: M=MgZ$^1$, Z$^1$=Cl, R=THP) and tetrahydro-2-(6-isopropenyl-3-methyl-9-decenyloxy)-2H-pyran (3: R=THP)

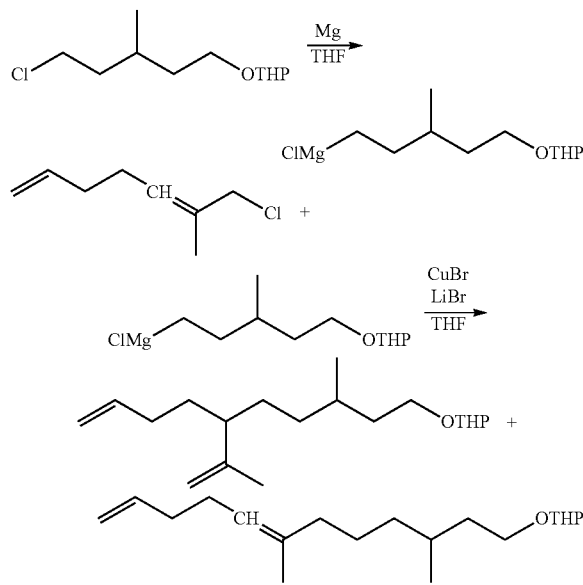

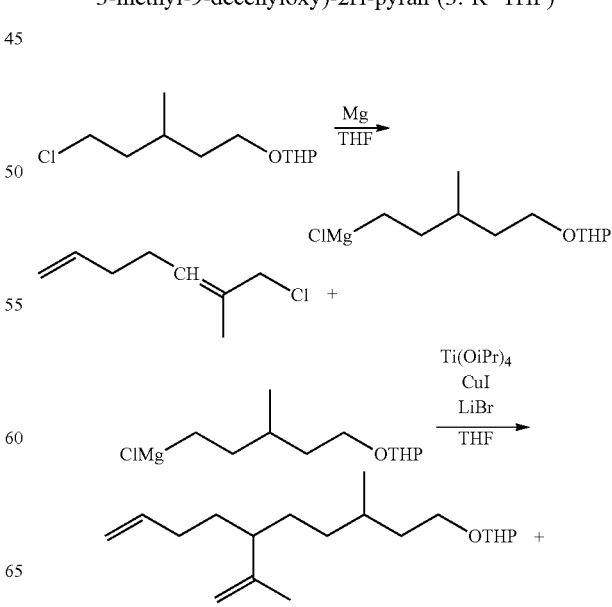

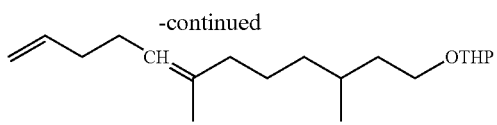

In a reactor were placed magnesium (0.26 g: 0.01 mol) and tetrahydrofuran (THF) (1 g) in a nitrogen atmosphere, heated to 60° C., and stirred for 10 minutes. Then, a mixed solution of tetrahydro-2-(5-chloro-3-methylpentyloxy)-2H-pyran (2.21 g: 0.01 mol) and tetrahydrofuran (THF) (2 g) was added dropwise into the reactor over 5 minutes. After the completion of the dropwise addition, the mixture was stirred at an internal temperature of 50 to 60° C. for 3 hours to obtain 3-methyl-5-(tetrahydropyran-2-yloxy)pentylmagnesium chloride (2: M=MgZ$^1$, Z$^1$=Cl, R=THP). Then, 3-methyl-5-(tetrahydropyran-2-yloxy)pentylmagnesium chloride (2: M=MgZ$^1$, Z$^1$=Cl, R=THP) thus obtained was cooled to room temperature.

In another reactor were placed titanium tetraisopropoxide (Ti(OiPr)$_4$) (2.89 g) and tetrahydrofuran (THF) (10 ml) in a nitrogen atmosphere and cooled to −10 to −5° C. The whole amount of 3-methyl-5-(tetrahydropyran-2-yloxy)pentylmagnesium chloride (2) prepared above was then added dropwise into the another reactor at −5° C. or below over 15 minutes. After the completion of the dropwise addition, a mixed solution of copper(I) iodide (CuI) (0.10 g), lithium bromide (LiBr) (0.09 g), and THF (10 ml) was added dropwise into the another reactor at −5° C. or below over 2 minutes. After the completion of the dropwise addition, 2-methyl-2,6-heptadienyl chloride (1: X=Cl) (1.45 g: 0.009 mol) obtained according to Example 4 was added dropwise at −5° C. or below over 20 minutes. After the completion of the dropwise addition, the mixture was stirred at −10 to −5° C. for 2 hours and further at room temperature for 24 hours. Pure water (20 g) and an aqueous solution of ammonium chloride (2 g) were added into the another reactor and stirred for 30 minutes, and then the organic phase was separated. The separated organic phase was subjected to post-treatment, i.e., washing, drying, and concentration, to obtain a crude product, tetrahydro-2-(6-isopropenyl-3-methyl-9-decenyloxy)-2H-pyran (3: R=THP) (2.13 g: 0.004 mol) in a crude yield of 50.0%. A production ratio of tetrahydro-2-(6-isopropenyl-3-methyl-9-decenyloxy)-2H-pyran (3: R=THP):tetrahydro-2-(3,7-dimethyl-7,11-dodecadienyloxy)-2H-pyran was 94:6.

The spectrum data of tetrahydro-2-(6-isopropenyl-3-methyl-9-decenyloxy)-2H-pyran (3: R=THP) thus obtained were same as those obtained in Example 5.

Example 9

Preparation of 3-methyl-5-(tetrahydropyran-2-yloxy)pentylmagnesium chloride (2: M=MgZ$^1$, Z$^1$=Cl, R=THP) and tetrahydro-2-(6-isopropenyl-3-methyl-9-decenyloxy)-2H-pyran (3: R=THP)

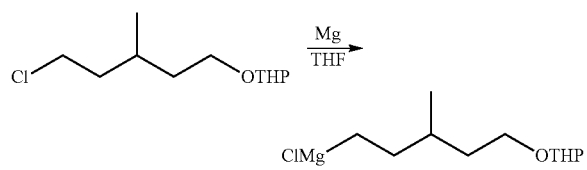

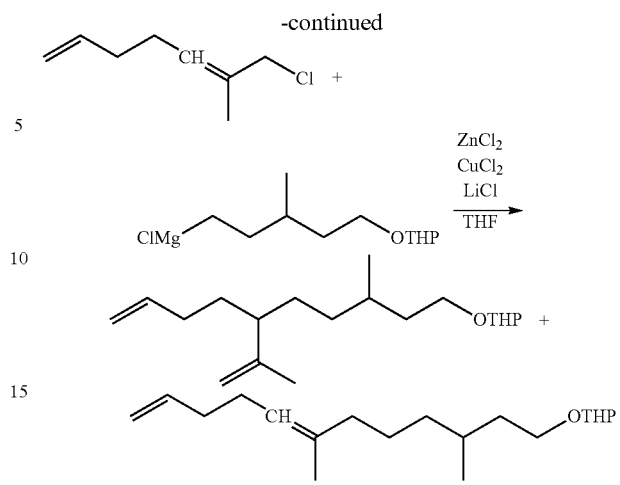

In a reactor were placed magnesium (0.087 g: 0.0035 mol) and tetrahydrofuran (THF) (0.3 g) in a nitrogen atmosphere, heated to 60° C., and stirred for 5 minutes. Then, a mixed solution of tetrahydro-2-(5-chloro-3-methylpentyloxy)-2H-pyran (0.74 g: 0.003 mol) and tetrahydrofuran (THF) (0.7 g) was added dropwise into the reactor over 15 minutes. After the completion of the dropwise addition, the mixture was stirred at an internal temperature of 50 to 60° C. for 3 hours to obtain 3-methyl-5-(tetrahydropyran-2-yloxy)pentylmagnesium chloride (2: M=MgZ$^1$, Z$^1$=Cl, R=THP). Then, 3-methyl-5-(tetrahydropyran-2-yloxy)pentylmagnesium chloride (2: M=MgZ$^1$, Z$^1$=Cl, R=THP) thus obtained was cooled to −5 to 5° C.

Zinc chloride (ZnCl$_2$) (0.08 g), copper (II) chloride (CuCl$_2$) (0.08 g), and lithium chloride (LiCl) (0.05 g) were added into the reactor, and then a mixed solution of 2-methyl-2,6-heptadienyl chloride (1: X=Cl) (0.50 g: 0.003 mol) obtained according to Example 4 and THF (10 ml) was added dropwise over 10 minutes. After the completion of the dropwise addition, the mixture was stirred at −5 to 5° C. for 5 hours. Pure water (20 g) and an aqueous solution of ammonium chloride (2 g) were added into the reactor and stirred for 30 minutes, and then the organic phase was separated. The separated organic phase was subjected to post-treatment, i.e., washing, drying, and concentration, to obtain a crude product, tetrahydro-2-(6-isopropenyl-3-methyl-9-decenyloxy)-2H-pyran (3: R=THP) (1.86 g: 0.003 mol) in a crude yield of 50.0%. A production ratio of tetrahydro-2-(6-isopropenyl-3-methyl-9-decenyloxy)-2H-pyran (3: R=THP):tetrahydro-2-(3,7-dimethyl-7,11-dodecadienyloxy)-2H-pyran was 78:22.

The spectrum data of tetrahydro-2-(6-isopropenyl-3-methyl-9-decenyloxy)-2H-pyran (3: R=THP) thus obtained were same as those obtained in Example 5.

Example 10

Preparation of 5-(1-ethoxyethoxy)-3-methylpentylmagnesium chloride (2: M=MgZ$^1$, Z$^1$=Cl, R=ethoxyethyl group (EE)) and tetrahydro-2-(6-isopropenyl-3-methyl-9-decenyloxy)-2H-pyran (3: R=EE)

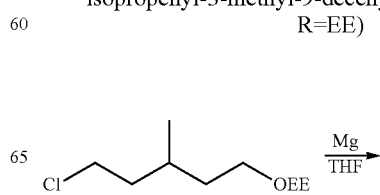

-continued

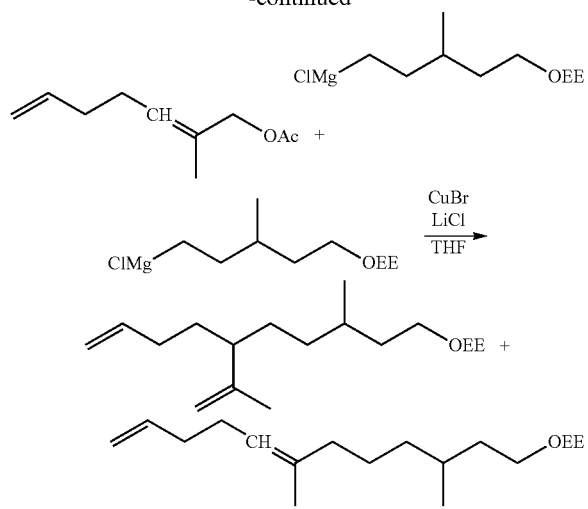

In a reactor were placed magnesium (31.84 g: 1.31 mol) and tetrahydrofuran (THF) (126 g) in a nitrogen atmosphere, heated to 60° C., and stirred for 40 minutes. Then, a mixed solution of 5-chloro-1-(1-ethoxyethoxy)-3-methylpentane (262.83 g: 1.26 mol) and tetrahydrofuran (THF) (252 g) was added dropwise into the reactor over 5 hours. After the completion of the dropwise addition, the mixture was stirred at an internal temperature of 60 to 70° C. for 3 hours to obtain 5-(1-ethoxyethoxy)-3-methylpentylmagnesium chloride (2: $M=MgZ^1$, $Z^1=Cl$, R=EE). Then, 5-(1-ethoxyethoxy)-3-methylpentylmagnesium chloride (2: $M=MgZ^1$, $Z^1=Cl$, R=EE) thus obtained was cooled to room temperature.

In another reactor were placed copper(I) bromide (CuBr) (72.30 g), lithium chloride (LiCl) (42.73 g), and tetrahydrofuran (THF) (756 g) in a nitrogen atmosphere, stirred at room temperature for 15 minutes, and cooled to 0 to 10° C. Then, 2-methyl-2,6-heptadienyl acetate (1': X'=OAc) (144.32 g: 0.84 mol) obtained according to Example 1 was added into the another reactor, stirred, and cooled to −5° C. to 5° C. The whole amount of 5-(1-ethoxyethoxy)-3-methylpentylmagnesium chloride (2: $M=MgZ^1$, $Z^1=Cl$, R=EE) prepared above was then added dropwise into the another reactor at −5 to 5° C. over 11 hours and 35 minutes. After the completion of the dropwise addition, the mixture was stirred at 10 to 15° C. for 2 hours and further at room temperature for 12 hours. A mixture of pure water (630 g), ammonium chloride (63 g), and an aqueous 20 wt. % hydrogen chloride solution (126 g) was added into the another reactor, and then n-hexane (500 ml) was added and stirred for 30 minutes. The organic phase was then separated. The separated organic phase was subjected to post-treatment, i.e., washing, drying, and concentration, to obtain a crude product, 1-(1-ethoxyethoxy)-6-isopropenyl-3-methyl-9-decene (3: R=EE) (320.21 g: 0.623 mol) in a crude yield of 74.17%. A production ratio of 1-(1-ethoxyethoxy)-6-isopropenyl-3-methyl-9-decene (3: R=EE):1-(1-ethoxyethoxy)-3,7-dimethyl-7,11-dodecadiene (3': R=EE) was 96:4.

The following are spectrum data of 1-(1-ethoxyethoxy)-6-isopropenyl-3-methyl-9-decene (3: R=EE) thus obtained.

IR (D-ATR): ν=3074, 2975, 2928, 2872, 1643, 1453, 1377, 1339, 1134, 1101, 1087, 1062, 992, 932, 909, 889, 845, 640, 554 cm$^{-1}$.

$^1$H-NMR (500 MHz, CDCl$_3$): δ=0.86-0.88 (3H, m), 0.98-1.08 (1H, m), 1.16-1.69 (17H, m), 1.89-2.07 (3H, m), 3.38-3.50 (2H, m), 3.51-3.73 (2H, m), 4.64-4.69 (2H, m), 4.72-4.74 (1H, m), 4.90-5.00 (2H, m), 5.75-5.83 (1H, m) ppm.

$^{13}$C-NMR (125 MHz, CDCl$_3$): δ=15.30, 17.69, 17.80, 19.47, 19.52, 19.76, 19.80, 19.85, 29.75, 29.80, 29.94, 29.97, 30.52, 30.65, 31.66, 32.58, 32.73, 34.68, 34.73, 34.81, 34.86, 36.62, 36.86, 36.98, 37.00, 46.99, 47.02, 47.11, 47.13, 60.58, 60.59, 63.40, 99.46, 99.50, 99.52, 111.65, 111.74, 114.15, 139.06, 147.19, 147.31 ppm.

GC-MS (EI, 70 eV): 29, 45, 59, 73, 95, 109, 123, 149, 163, 177, 194, 208, 237, 267, 282.

Example 11

Preparation of 5-(1-ethoxyethoxy)-3-methylpentylmagnesium chloride (2: $M=MgZ^1$, $Z^1=Cl$, R=EE) and tetrahydro-2-(6-isopropenyl-3-methyl-9-decenyloxy)-2H-pyran (3: R=EE)

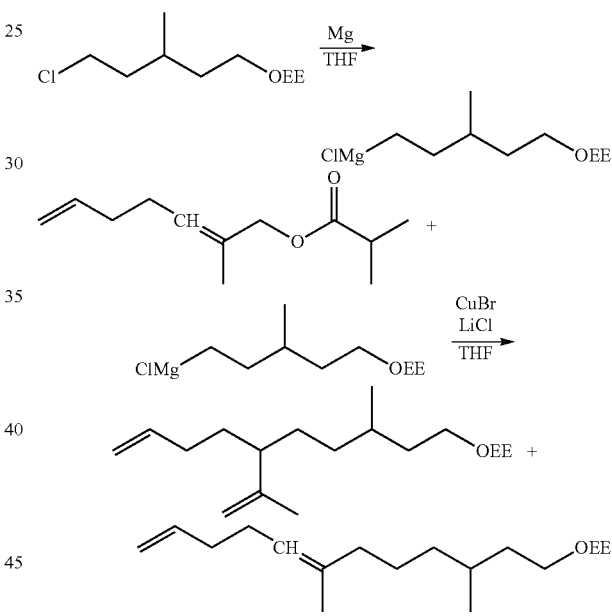

In a reactor were placed magnesium (3.49 g: 0.14 mol) and tetrahydrofuran (THF) (13.8 g) in a nitrogen atmosphere, heated to 60° C., and stirred for 5 minutes. Then, a mixed solution of 5-chloro-1-(1-ethoxyethoxy)-3-methylpentane (30.82 g: 0.14 mol) and tetrahydrofuran (THF) (27.6 g) was added dropwise into the reactor over 100 minutes. After the completion of the dropwise addition, the mixture was stirred at an internal temperature of 60 to 70° C. for 6 hours to obtain 5-(1-ethoxyethoxy)-3-methylpentylmagnesium chloride (2: $M=MgZ^1$, $Z^1=Cl$, R=EE). Then, 5-(1-ethoxyethoxy)-3-methylpentylmagnesium chloride (2: $M=MgZ^1$, $Z^1=Cl$, R=EE) thus obtained was cooled to room temperature.

In another reactor were placed copper(I) bromide (CuBr) (7.92 g), lithium chloride (LiCl) (4.68 g), and tetrahydrofuran (THF) (82.80 g) in a nitrogen atmosphere, stirred at room temperature for 100 minutes, and cooled to 10° C. to 15° C. Then, 2-methyl-2,6-heptadienyl isobutyrate (1: X=isobutyryloxy) (20.00 g: 0.09 mol) obtained according to Example 2 was added into the another reactor and stirred. The whole amount of 5-(1-ethoxyethoxy)-3-methylpentylmagnesium chloride (2: M=MgZ$^1$, Z$^1$=Cl, R=EE) prepared above was then added dropwise into the another reactor at 10 to 15° C. over 4 hours. After the completion of the dropwise addition, the mixture was stirred at 10 to 15° C. for 18 hours. A mixture of pure water (41 g), ammonium chloride (4.1 g), and an aqueous 20 wt. % hydrogen chloride solution (13.8 g) was then added into the another reactor. n-Hexane (138 g) was added and stirred for 30 minutes, and then the organic phase was separated. The separated organic phase was subjected to post-treatment, i.e., washing, drying, and concentration, to obtain a crude product, 1-(1-ethoxyethoxy)-6-isopropenyl-3-methyl-9-decene (3) (36.04 g) in a crude yield of 54.44%. A production ratio of 1-(1-ethoxyethoxy)-6-isopropenyl-3-methyl-9-decene (2: M=MgZ$^1$, Z$^1$=Cl, R=EE):1-(1-ethoxyethoxy)-3,7-dimethyl-7,11-dodecadiene was 65:35.

Example 12

Preparation of 2-methyl-2,6-heptadienyl methanesulfonate (1″: X″=OMs), 5-(1-ethoxyethoxy)-3-methylpentylmagnesium chloride (2: M=MgZ$^1$, Z$^1$=Cl, R=EE), and tetrahydro-2-(6-isopropenyl-3-methyl-9-decenyloxy)-2H-pyran (3: R=EE)

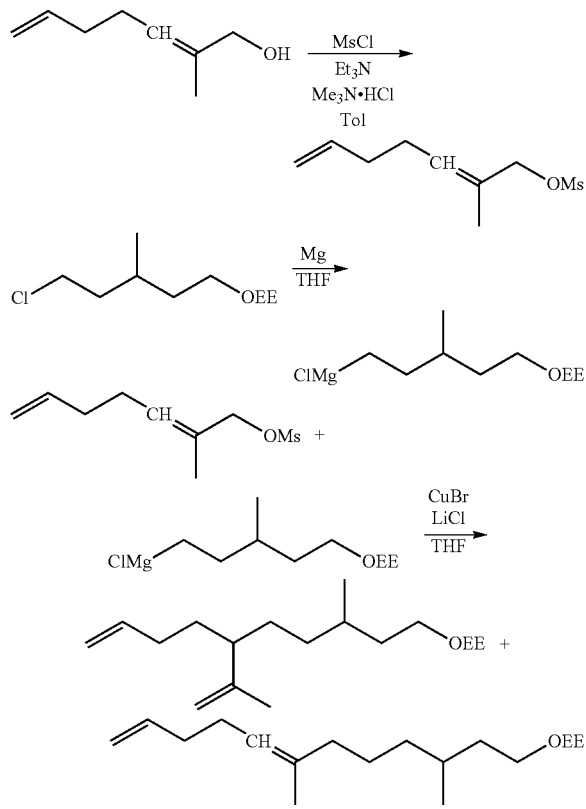

In a reactor were placed 2-methyl-2,6-heptadienol (10.00 g: 0.074 mol), triethylamine (11.23 g: 0.111 mol), and toluene (65 g) in a nitrogen atmosphere, and the mixture was cooled to an internal temperature of −5 to 5° C. and stirred for 20 minutes. Then, a mixed solution of methanesulfonyl chloride (MsCl) (12.71 g: 0.111 mol) and toluene (80 g) was added dropwise into the reactor over 90 minutes with the internal temperature being kept at −5 to 5° C. After the completion of the dropwise addition, the mixture was stirred at an internal temperature of −5 to 5° C. for 8 hours. Then, pure water (130 g) was added into the reactor and stirred for 30 minutes, and then the organic phase was separated. The separated organic phase was subjected to post-treatment, i.e., washing, drying, and filtration, to obtain a toluene solution (190.97 g) containing a crude product, 2-methyl-2,6-heptadienyl methanesulfonate (1″: X″=OMs).

The following are the Rf value in thin layer chromatography and spectrum data of the crude product, 2-methyl-2,6-heptadienyl methanesulfonate (1″: X″=OMs) thus obtained.

Thin layer chromatography (TLC): Rf=0.19 (hexane: ethyl acetate=10:1)

$^1$H-NMR (500 MHz, CDCl$_3$): δ=1.83 (3H, s-like), 2.11-2.25 (4H, m), 3.00 (3H, s), 4.75 (2H, s), 4.98-5.09 (2H, m), 5.54 (1H, t-like, J=7.3 Hz), 5.75-5.84 (1H, m) ppm.

GC-MS (EI, 70 eV): 27, 41, 55, 67, 79, 93, 108, 121, 135, 150, 163, 176, 204.

In a reactor were placed magnesium (2.96 g: 0.12 mol) and tetrahydrofuran (THF) (11.7 g) in a nitrogen atmosphere, heated to 60° C., and stirred for 10 minutes. Then, a mixed solution of 5-chloro-1-(1-ethoxyethoxy)-3-methylpentane (26.13 g: 0.12 mol) and tetrahydrofuran (THF) (23.4 g) was added dropwise into the reactor over 115 minutes. After the completion of the dropwise addition, the mixture was stirred at an internal temperature of 60 to 70° C. for 2 hours to obtain 5-(1-ethoxyethoxy)-3-methylpentylmagnesium chloride (2: M=MgZ$^1$, Z$^1$=Cl, R=EE). Then, 5-(1-ethoxyethoxy)-3-methylpentylmagnesium chloride (2: M=MgZ$^1$, Z$^1$=Cl, R=EE) thus obtained was cooled to room temperature.

In another reactor were placed copper(I) bromide (CuBr) (5.59 g), lithium chloride (LiCl) (3.31 g), and tetrahydrofuran (THF) (35.10 g) in a nitrogen atmosphere, stirred at room temperature for 90 minutes, and then cooled to 10° C. to 15° C. Then, a toluene solution (100.00 g) containing the obtained crude product, 2-methyl-2,6-heptadienyl methanesulfonate (1: X=OMs) was added into the another reactor and stirred. The whole amount of 5-(1-ethoxyethoxy)-3-methylpentylmagnesium chloride (2: M=MgZ$^1$, Z$^1$=Cl, R=EE) prepared above was then added dropwise into the another reactor at −5 to 5° C. over 3 hours. After the completion of the dropwise addition, the mixture was stirred at 10 to 15° C. for 14 hours. A mixture of pure water (100 g), ammonium chloride (4 g), and an aqueous 20 wt. % hydrogen chloride solution (4 g) was added into the another reactor. Then, n-hexane (100 g) was added and stirred for 30 minutes, and the organic phase was separated. The separated organic phase was subjected to post-treatment, i.e., washing, drying, and concentration, to obtain a crude product, 1-(1-ethoxyethoxy)-6-isopropenyl-3-methyl-9-decene (3: R=EE) (21.55 g). A crude yield was 30.77% on a basis of 2-methyl-2,6-heptadienol. A production ratio of 1-(1-ethoxyethoxy)-6-isopropenyl-3-methyl-9-decene (3: R=EE):1-(1-ethoxyethoxy)-3,7-dimethyl-7,11-dodecadiene was 63:37.

Example 13

Preparation of 2-methyl-2,6-heptadienyl p-toluenesulfonate (1″: X″=p-toluenesulfonyloxy group (OTs)), 5-(1-ethoxyethoxy)-3-methylpentylmagnesium chloride (2: M=MgZ$^1$, Z$^1$=Cl, R=EE), and tetrahydro-2-(6-isopropenyl-3-methyl-9-decenyloxy)-2H-pyran (3: R=EE)

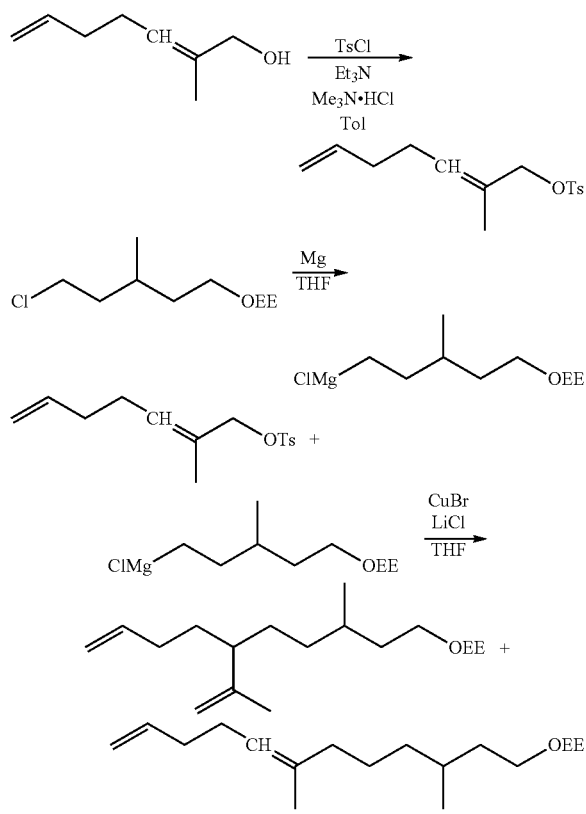

In a reactor were placed 2-methyl-2,6-heptadienol (10.00 g: 0.074 mol), triethylamine (11.23 g: 0.111 mol), and toluene (65 g) in a nitrogen atmosphere, cooled to an internal temperature of −5 to 5° C., and stirred for 50 minutes. Then, a mixed solution of p-toluenesulfonyl chloride (TsCl) (21.16 g: 0.111 mol) and toluene (80 g) was added dropwise into the reactor over 90 minutes with the internal temperature being kept at −5 to 5° C. After the completion of the dropwise addition, the mixture was stirred at an internal temperature of −5 to 5° C. for 7 hours. Then, pure water (130 g) was added into the reactor and stirred for 30 minutes, and the organic phase was separated. The separated organic phase was subjected to post-treatment, i.e., washing, drying, and filtration, to obtain a toluene solution (185.69 g) containing a crude product, 2-methyl-2,6-heptadienyl p-toluenesulfonate (1″: X″=OTs).

The following are the Rf value in thin layer chromatography and spectrum data of the crude product, 2-methyl-2,6-heptadienyl p-toluenesulfonate (1″: X″=OTs) thus obtained.

Thin layer chromatography (TLC): Rf=0.21 (hexane:ethyl acetate=10:1)

$^1$H-NMR (500 MHz, CDCl$_3$): δ=1.70 (3H, s-like), 2.00-2.08 (4H, m), 2.46 (3H, s), 4.55 (2H, s), 4.96-5.01 (2H, m), 5.41-5.44 (1H, m), 5.69-5.78 (1H, m), 7.35 (2H, d, J=8.0 Hz), 7.82 (2H, d, J=8.4 Hz) ppm.

In a reactor were placed magnesium (3.03 g: 0.12 mol) and tetrahydrofuran (THF) (12.0 g) in a nitrogen atmosphere, heated to 60° C., and stirred for 10 minutes. Then, a mixed solution of 5-chloro-1-(1-ethoxyethoxy)-3-methylpentane (26.80 g: 0.12 mol) and tetrahydrofuran (THF) (24.0 g) was added dropwise into the reactor over 120 minutes. After the completion of the dropwise addition, the mixture was stirred at an internal temperature of 60 to 70° C. for 2 hours to obtain 5-(1-ethoxyethoxy)-3-methylpentylmagnesium chloride (2: M=MgZ$^1$, Z$^1$=Cl, R=EE). Then, 5-(1-ethoxyethoxy)-3-methylpentylmagnesium chloride (2: M=MgZ$^1$, Z$^1$=Cl, R=EE) thus obtained was cooled to room temperature.

In another reactor were placed copper(I) bromide (CuBr) (5.74 g), lithium chloride (LiCl) (3.39 g), and tetrahydrofuran (THF) (36.00 g) in a nitrogen atmosphere, stirred at room temperature for 120 minutes, and then cooled to 10° C. to 15° C. Then, a toluene solution (100.00 g) containing the obtained crude product, 2-methyl-2,6-heptadienyl p-toluenesulfonate (1″: X″=OTs) was added into the another reactor and stirred. The whole amount of 5-(1-ethoxyethoxy)-3-methylpentylmagnesium chloride (2: M=MgZ$^1$, Z$^1$=Cl, R=EE) prepared above was then added dropwise into the another reactor at −5 to 5° C. over 3 hours. After the completion of the dropwise addition, the mixture was stirred at 10 to 15° C. for 14 hours. A mixture of pure water (100 g), ammonium chloride (4 g), and an aqueous 20 wt. % hydrogen chloride solution (4 g) was then added into the another reactor. n-Hexane (100 g) was added and stirred for 30 minutes, and then the organic phase was separated. The separated organic phase was subjected to post-treatment, i.e., washing, drying, and concentration, to obtain a crude product, 1-(1-ethoxyethoxy)-6-isopropenyl-3-methyl-9-decene (3: R=EE) (25.55 g). A crude yield was 43.30% on a basis of 2-methyl-2,6-heptadienol. A production ratio of 1-(1-ethoxyethoxy)-6-isopropenyl-3-methyl-9-decene (3: R=EE):1-(1-ethoxyethoxy)-3,7-dimethyl-7,11-dodecadiene was 59:41.

The spectrum data of 1-(1-ethoxyethoxy)-6-isopropenyl-3-methyl-9-decene (3: R=EE) thus obtained were same as those obtained in Example 10.

Example 14

Preparation of 5-(t-butyldimethylsilyloxy)-3-methylpentylmagnesium chloride (2: M=MgZ$^1$, Z$^1$=Cl, R=tert-butyldimethylsilyl (TBS)) and 1-(t-butyldimethylsilyloxy)-6-isopropenyl-3-methyl-9-decene (3: R=TBS)

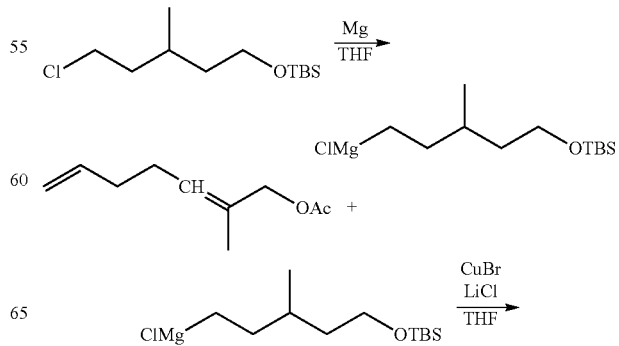

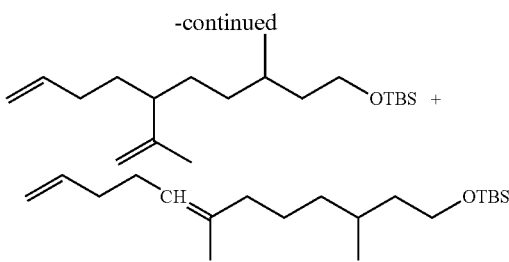

In a reactor were placed magnesium (1.07 g: 0.044 mol) and tetrahydrofuran (THF) (4.2 g) in a nitrogen atmosphere, heated to 60° C., and stirred for 50 minutes. Then, a mixed solution of 5-chloro-1-(t-butyldimethylsilyloxy)-3-methylpentane (10.80 g: 0.042 mol) and tetrahydrofuran (THF) (8.4 g) was added dropwise into the reactor over 40 minutes. After the completion of the dropwise addition, the mixture was stirred at an internal temperature of 60 to 70° C. for 4 hours to obtain 5-(t-butyldimethylsilyloxy)-3-methylpentylmagnesium chloride (2: $M=MgZ^1$, $Z^1=Cl$, R=TBS). Then, 5-(t-butyldimethylsilyloxy)-3-methylpentylmagnesium chloride (2: $M=MgZ^1$, $Z^1=Cl$, R=TBS) thus obtained was cooled to room temperature.

In another reactor were placed copper(I) bromide (CuBr) (2.32 g), lithium chloride (LiCl) (1.37 g), and tetrahydrofuran (THF) (24.4 g) in a nitrogen atmosphere, stirred at room temperature for 10 minutes, and then cooled to 0 to 10° C. Then, 2-methyl-2,6-heptadienyl acetate (1': X'=OAc) (4.66 g: 0.027 mol) was added into the another reactor, stirred, and cooled to 0° C. to 5° C. The whole amount of 5-(t-butyldimethylsilyloxy)-3-methylpentylmagnesium chloride (2) prepared above was then added dropwise into the another reactor at −5 to 5° C. over 3 hours. After the completion of the dropwise addition, the mixture was stirred at 10 to 15° C. for 15 hours. A mixture of pure water (13.5 g), ammonium chloride (1.35 g), and an aqueous 20 wt. % hydrogen chloride solution (4.59 g) was added into the another reactor. Toluene (10 g) was added and stirred for 30 minutes, and then the organic phase was separated. The separated organic phase was subjected to post-treatment, i.e., washing, drying, and concentration, to obtain a crude product, 1-(t-butyldimethylsilyloxy)-6-isopropenyl-3-methyl-9-decene (3: R=TBS) (11.89 g) in a crude yield of 55.56%. A production ratio of 1-(t-butyldimethylsilyloxy)-6-isopropenyl-3-methyl-9-decene (3: R=TB S):1-(t-butyldimethylsilyloxy)-3,7-dimethyl-7,11-dodecadiene was 75:25.

The following are spectrum data of 1-(t-butyldimethylsilyloxy)-6-isopropenyl-3-methyl-9-decene (3: R=TBS) thus obtained.

IR (D-ATR): ν=3074, 2955, 2928, 2857, 1643, 1472, 1462, 1376, 1361, 1255, 1097, 1005, 992, 939, 909, 890, 836, 811, 775, 731, 662 cm$^{-1}$.

$^1$H-NMR (500 MHz, CDCl$_3$): δ=0.05 (6H, s), 0.84-0.87 (3H, m), 0.89 (9H, s), 0.98-1.09 (1H, m), 1.15-1.1.43 (6H, m), 1.46-1.61 (5H, m), 1.88-2.04 (3H, m), 3.58-3.68 (2H, m), 4.66 (1H, s-like), 4.73-4.75 (1H, m), 4.91-5.01 (2H, m), 5.76-5.84 (1H, m) ppm.

$^{13}$C-NMR (125 MHz, CDCl$_3$): δ=−5.29, 17.72, 17.81, 18.33, 19.58, 19.89, 25.97, 29.42, 29.54, 30.61, 30.69, 31.70, 32.61, 32.75, 34.78, 34.86, 39.72, 40.12, 47.02, 47.11, 61.45, 61.47, 111.65, 111.73, 114.14, 139.11, 147.25, 147.36 ppm.

GC-MS (EI, 70 eV): 29, 55, 75, 95, 113, 129, 157, 173, 191, 213, 233, 249, 267.

Example 15

Preparation of 6-isopropenyl-3-methyl-9-decenol (4)

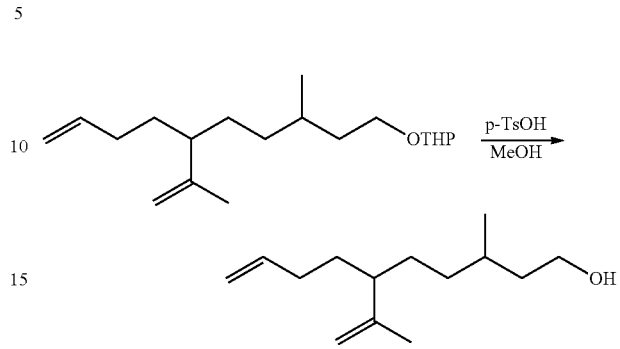

In a reactor were placed tetrahydro-2-(6-isopropenyl-3-methyl-9-decenyloxy)-2H-pyran (3: R=THP) (27.47 g: 0.69 mol) obtained according to Example 7, p-toluenesulfonic acid (5.36 g), and methanol (93 g) in a nitrogen atmosphere, and stirred at an internal temperature of 50 to 60° C. for 4 hours. After the completion of the stirring, the solvent was removed by concentration. Methanol (93 g) was then added into the reactor and stirred at room temperature for 12 hours. The mixture was then stirred at an internal temperature of 50 to 60° C. for 2 hours, and the solvent was removed by concentration. Then, pure water (150 g) and n-hexane (100 g) were added into the reactor and stirred for 30 minutes, and then the organic phase was separated. The separated organic phase was subjected to post-treatment, i.e., washing, drying, and concentration, to obtain a crude product, 6-isopropenyl-3-methyl-9-decenol (4) (18.46 g) in a crude yield of 72.46%.

The following are spectrum data of 6-isopropenyl-3-methyl-9-decenol (4) thus obtained.

IR (D-ATR): ν=3332, 3074, 2928, 2871, 1642, 1452, 1376, 1058, 994, 909, 889, 641 cm$^{-1}$.

$^1$H-NMR (500 MHz, CDCl$_3$): δ=0.87-0.90 (3H, m), 1.00-1.09 (1H, m), 1.17-1.69 (12H, m), 1.87-2.08 (3H, m), 3.60-3.70 (2H, m), 4.66 (1H, s-like), 4.74 (1H, s-like), 4.90-5.02 (2H, m), 5.75-5.84 (1H, m) ppm.

$^{13}$C-NMR (125 MHz, CDCl$_3$): δ=17.63, 17.79, 18.52, 19.77, 29.29, 29.61, 30.46, 30.64, 30.65, 32.56, 32.74, 34.62, 34.88, 39.63, 40.04, 46.91, 47.10, 61.11, 61.14, 111.70, 111.81, 114.17, 139.04, 139.06, 147.21, 147.28 ppm.

GC-MS (EI, 70 eV): 29, 41, 55, 69, 81, 95, 109, 123, 135, 149, 167, 182, 195, 210.

Example 16

Preparation of 6-isopropenyl-3-methyl-9-decenol (4)

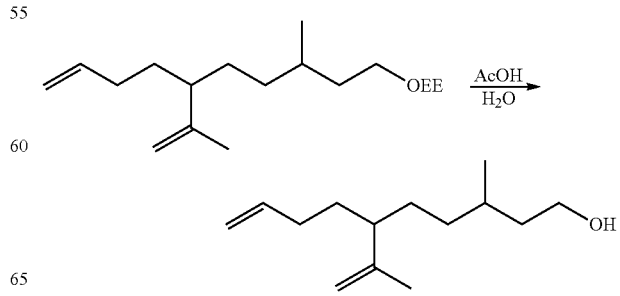

In a reactor were placed 1-(1-ethoxyethoxy)-6-isopropenyl-3-methyl-9-decene (3: R=EE) (273.79 g: 0.59 mol), acetic acid (35.52 g), tetrahydrofuran (THF) (250 g), and pure water (266.4 g) in a nitrogen atmosphere and stirred at an internal temperature of 70 to 80° C. for 7 hours. Then, the content of the reactor was cooled to room temperature, and pure water (500 g) and toluene (200 g) were added and stirred for 30 minutes. The organic phase was then separated. The separated organic phase was subjected to post-treatment, i.e., washing, drying, and concentration, to obtain a crude product, 6-isopropenyl-3-methyl-9-decenol (4) (216.33 g) in a crude yield of 100%.

The spectrum data of 6-isopropenyl-3-methyl-9-decenol (4) thus obtained were same as those obtained in Example 15.

Example 17

Preparation of 6-isopropenyl-3-methyl-9-decenol (4)

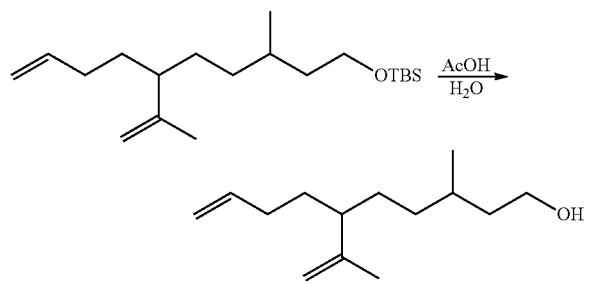

In a reactor were placed 1-(t-butyldimethylsilyloxy)-6-isopropenyl-3-methyl-9-decene (3: R=TBS) (2.00 g: 0.003 mol) obtained according to Example 14 and tetrahydrofuran (THF) (30 g) in a nitrogen atmosphere and stirred at room temperature for 5 minutes. Then, a THF solution of tetrabutylammonium fluoride (5.4 mL: 0.005 mol) was added dropwise into the reactor over 10 minutes. After the completion of the dropwise addition, the mixture was stirred at room temperature for 5 hours. Pure water (30 g), sodium chloride (3 g), and n-hexane (30 g) were then added into the reactor and stirred for 30 minutes, and the organic phase was separated. The separated organic phase was subjected to post-treatment, i.e., washing, drying, and concentration, to obtain a crude product, 6-isopropenyl-3-methyl-9-decenol (4) (1.99 g) in a crude yield of 100%.

The spectrum data of 6-isopropenyl-3-methyl-9-decenol (4) thus obtained were same as those obtained in Example 15.

Example 18

Preparation of 6-isopropenyl-3-methyl-9-decenyl acetate (5)

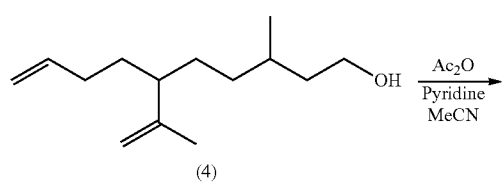

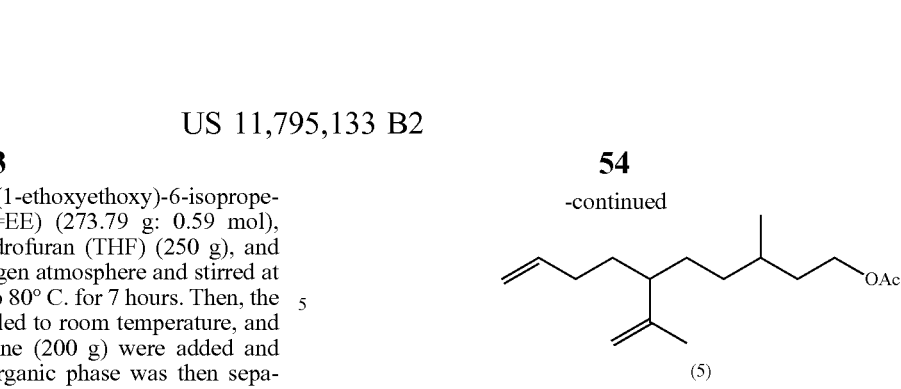

In a reactor were placed 6-isopropenyl-3-methyl-9-decenol (4) (215.33 g: 0.77 mol) obtained according to Example 16, pyridine (213.45 g), acetic anhydride (131.78 g), and acetonitrile (220 g) in a nitrogen atmosphere and stirred at room temperature for 4 hours and 45 minutes. Then, pure water (600 g) and n-hexane (300 g) were added into the reactor and stirred for 30 minutes, and the organic phase was separated. The separated organic phase was subjected to post-treatment, i.e., washing, drying, and concentration, to obtain a crude product, 6-isopropenyl-3-methyl-9-decenyl acetate (5) (245.31 g). This crude product was subjected to distillation at a reduced pressure to obtain the target compound, 6-isopropenyl-3-methyl-9-decenyl acetate (5) (142.32 g: 0.55 mol). A yield from the whole fractions including a first fraction was 83.27%.

The following are spectrum data of 6-isopropenyl-3-methyl-9-decenyl acetate (5) thus obtained.

IR (D-ATR): ν=3073, 2928, 2871, 1742, 1642, 1454, 1367, 1239, 1037, 995, 909, 889, 636, 606 cm$^{-1}$.

$^1$H-NMR (500 MHz, CDCl$_3$): δ=0.87-0.90 (3H, m), 1.01-1.09 (1H, m), 1.18-1.54 (7H, m), 1.56-1.58 (3H, m), 1.59-1.68 (1H, m), 1.89-2.01 (3H, m), 2.02 (3H, s), 4.01-4.12 (2H, m), 4.65 (1H, s-like), 4.74 (1H, s-like), 4.91-5.01 (2H, m), 5.74-5.83 (1H, m) ppm.

$^{13}$C-NMR (125 MHz, CDCl$_3$): δ=17.63, 17.77, 19.32, 19.63, 20.99, 29.68, 29.96, 30.43, 30.56, 31.62, 31.65, 32.56, 32.72, 34.49, 34.64, 35.19, 35.64, 46.89, 47.04, 62.98, 63.02, 111.77, 111.86, 114.19, 138.99, 147.03, 147.15, 171.16 ppm.

GC-MS (EI, 70 eV): 29, 43, 55, 67, 81, 95, 109, 123, 135, 149, 163, 177, 192, 209, 223, 237, 252.

Example 19

Preparation of 6-isopropenyl-3-methyl-9-decenyl acetate (5)

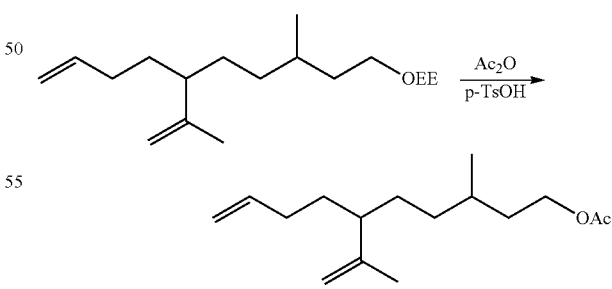

In a reactor were placed acetic anhydride (24.50 g) and p-toluenesulfonic acid (0.05 g) in a nitrogen atmosphere and stirred at room temperature for 5 minutes. Then, 1-(1-ethoxyethoxy)-6-isopropenyl-3-methyl-9-decene (3: R=EE) (10.00 g: 0.023 mol) obtained according to Example 10 was added dropwise into the reactor over 1 minute, and the mixture was stirred at an internal temperature of 90° C. for 6 hours. Then, pure water (10 g) and n-hexane (50 g) were added into the reactor and stirred for 30 minutes. After the completion of the stirring, the organic phase was separated. The separated organic phase was subjected to post-treatment, i.e., washing, drying, and concentration, to obtain a crude product, 6-isopropenyl-3-methyl-9-decenyl acetate (5) (9.50 g) in a crude yield of 100%.

The spectrum data of 6-isopropenyl-3-methyl-9-decenyl acetate (5) thus obtained were same as those obtained in Example 18.

The invention claimed is:

1. A process for preparing 6-isopropenyl-3-methyl-9-decenyl acetate of the following formula (5):

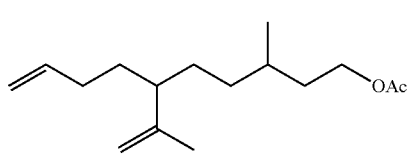

(5)

wherein Ac represents an acetyl group,
the process comprising steps of:
subjecting a 2-methyl-2,6-heptadiene compound of the following general formula (1) having a leaving group X at position 1:

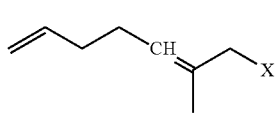

(1)

wherein X represents an acyloxy group having 1 to 10 carbon atoms including the carbon atom of the carbonyl group, an alkanesulfonyloxy group having 1 to 10 carbon atoms, an arenesulfonyloxy group having 6 to 20 carbon atoms, or a halogen atom,
to a nucleophilic substitution reaction with a 3-methylpentyl nucleophilic reagent of the following general formula (2) having a protected hydroxyl group at position 5:

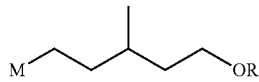

(2)

wherein M represents Li, MgZ$^1$, ZnZ$^1$, Cu, CuZ$^1$, or CuLiZ$^1$, wherein Z$^1$ represents a halogen atom or a CH$_2$CH$_2$CH(CH$_3$)CH$_2$CH$_2$OR group, and R represents a protecting group for a hydroxyl group,
to form a 6-isopropenyl-3-methyl-9-decene compound of the following general formula (3) having a protected hydroxyl group at position 1:

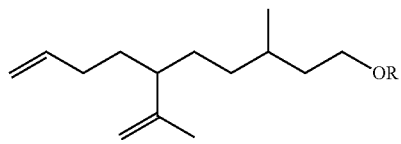

(3)

wherein R is as defined above;
subjecting the 6-isopropenyl-3-methyl-9-decene compound (3) having the protected hydroxyl group at position 1 to a deprotection reaction to form 6-isopropenyl-3-methyl-9-decenol of the following formula (4):

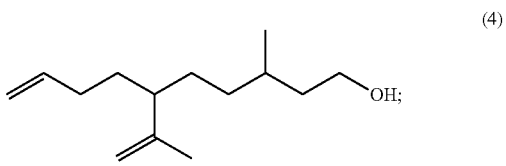

(4)

and
acetylating 6-isopropenyl-3-methyl-9-decenol (4) to form 6-isopropenyl-3-methyl-9-decenyl acetate (5).

2. The process for preparing 6-isopropenyl-3-methyl-9-decenyl acetate (5) according to claim 1, the process further comprising a step of:
converting a hydroxyl group of 2-methyl-2,6-heptadienol of the following formula (6):

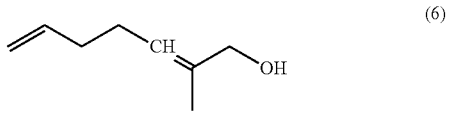

(6)

to X to form the 2-methyl-2,6-heptadiene compound (1) having the leaving group X at position 1, wherein X is as defined above.

3. A process for preparing 6-isopropenyl-3-methyl-9-decenyl acetate of the following formula (5):

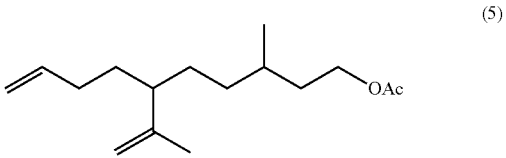

(5)

wherein Ac represents an acetyl group,
the process comprising steps of:
subjecting a 2-methyl-2,6-heptadiene compound of the following general formula (1) having a leaving group X at position 1:

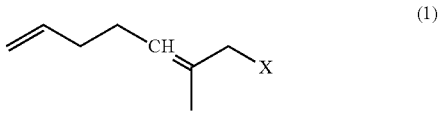

(1)

wherein X represents an acyloxy group having 1 to 10 carbon atoms including the carbon atom of the carbonyl group, an alkanesulfonyloxy group having 1 to 10 carbon atoms, an arenesulfonyloxy group having 6 to 20 carbon atoms, or a halogen atom,
to a nucleophilic substitution reaction with a 3-methylpentyl nucleophilic reagent of the following general formula (2) having a protected hydroxyl group at position 5:

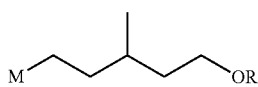

(2)

wherein M represents Li, MgZ$^1$, ZnZ$^1$, Cu, CuZ$^1$, or CuLiZ$^1$, wherein Z$^1$ represents a halogen atom or a CH$_2$CH$_2$CH(CH$_3$)CH$_2$CH$_2$OR group, and R represents a protecting group for a hydroxyl group, to form a 6-isopropenyl-3-methyl-9-decene compound of the following general formula (3) having a protected hydroxyl group at position 1:

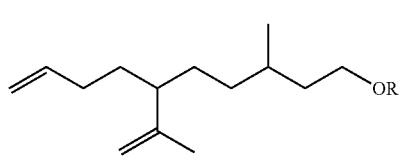

(3)

wherein R is as defined above; and subjecting the 6-isopropenyl-3-methyl-9-decene compound (3) having the protected hydroxyl group at position 1 to acetylation to form 6-isopropenyl-3-methyl-9-decenyl acetate (5).

4. The process for preparing 6-isopropenyl-3-methyl-9-decenyl acetate (5) according to claim 3, the process further comprising a step of:

converting the hydroxyl group of 2-methyl-2,6-heptadienol of the following formula (6):

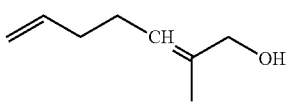

(6)

to X to form the 2-methyl-2,6-heptadiene compound (1) having a leaving group X at position 1, wherein X is as defined above.

5. A 2-methyl-2,6-heptadiene compound of the following general formula (1') having X' at position 1:

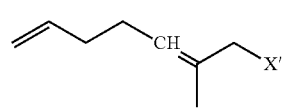

(1')

wherein X' represents an acyloxy group having 1 to 10 carbon atoms including the carbon atom of the carbonyl group, and the acyloxy group is selected from the group of consisting of a linear aliphatic acyloxy group and a branched aliphatic acyloxy group.

6. A 2-methyl-2,6-heptadiene compound of the following general formula (1″) having X″ at position 1:

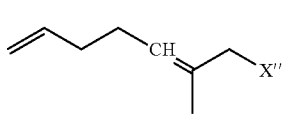

(1″)

wherein X″ represents an alkanesulfonyloxy group having 1 to 10 carbon atoms or an arenesulfonyloxy group having 6 to 20 carbon atoms.

7. The 2-methyl-2,6-heptadiene compound (1') having X' at position 1 according to claim 5, wherein the linear aliphatic acyloxy group is selected from the group consisting of a formyloxy group, an acetoxy group, a propanoyloxy group, a butanoyloxy group, a pentanoyloxy group, a hexanoyloxy group, a heptanoyloxy group, an octanoyloxy group, a nonanoyloxy group, a decanoyloxy group, and a crotonyloxy group, and isomers thereof.

8. The 2-methyl-2,6-heptadiene compound (1') having X' at position 1 according to claim 5, wherein the branched aliphatic acyloxy group is selected from the group consisting of a 2-methylpropanoyloxy group, a pivaloyloxy group, a 2-methylbutanoyloxy group, a 3-methyl-2-butenoyloxy group, and a 3-methyl-3-butenoyloxy group, and isomers thereof.

9. The 2-methyl-2,6-heptadiene compound (1') having X' at position 1 according to claim 5, wherein the linear aliphatic acyloxy group is selected from the group consisting of a formyloxy group, an acetoxy group, and a propanoyloxy group, and isomers thereof.

10. The 2-methyl-2,6-heptadiene compound (1') having X' at position 1 according to claim 5, wherein the branched aliphatic acyloxy group is selected from the group consisting of a 2-methylpropanoyloxy group, and a pivaloyloxy group, and isomers thereof.

* * * * *

UNITED STATES PATENT AND TRADEMARK OFFICE
CERTIFICATE OF CORRECTION

PATENT NO. : 11,795,133 B2
APPLICATION NO. : 17/368996
DATED : October 24, 2023
INVENTOR(S) : Baba et al.

It is certified that error appears in the above-identified patent and that said Letters Patent is hereby corrected as shown below:

In the Specification

Column 17, Line 35: Please correct "solvent" to read --solvent.--

Column 21, Line 61: Please correct "LiBF4" to read --LiBF$_4$--

Column 36, Line 16: Please correct "product]·[(weight" to read --product]÷[(weight--

Column 38, Line 51: Please correct "MSCl" to read --MsCl--

Column 40, Lines 6-7: Please remove the paragraph break between "(1.24 g:" and "0.04 mol)"

Signed and Sealed this
Twenty-sixth Day of March, 2024

Katherine Kelly Vidal
*Director of the United States Patent and Trademark Office*